(12) United States Patent
Place et al.

(10) Patent No.: US 9,045,751 B2
(45) Date of Patent: Jun. 2, 2015

(54) MODIFIED SMALL ACTIVATING RNA MOLECULES AND METHODS OF USE

(75) Inventors: Robert F. Place, San Francisco, CA (US); Long-Cheng Li, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 897 days.

(21) Appl. No.: 13/096,817

(22) Filed: Apr. 28, 2011

(65) Prior Publication Data

US 2015/0126578 A1    May 7, 2015

Related U.S. Application Data

(60) Provisional application No. 61/329,057, filed on Apr. 28, 2010.

(51) Int. Cl.
| | | |
|---|---|---|
| *C07H 21/02* | (2006.01) | |
| *C07H 21/04* | (2006.01) | |
| *A61K 48/00* | (2006.01) | |
| *C12N 15/113* | (2010.01) | |

(52) U.S. Cl.
CPC .......... *C12N 15/113* (2013.01); *C12N 2320/30* (2013.01); *C12N 2310/11* (2013.01)

(58) Field of Classification Search
CPC ..... A61K 48/00; C12N 15/111; C12N 15/113
See application file for complete search history.

(56) References Cited

U.S. PATENT DOCUMENTS

| | | | |
|---|---|---|---|
| 5,222,982 | A | 6/1993 | Ommaya |
| 5,385,582 | A | 1/1995 | Ommaya |
| 5,614,396 | A | 3/1997 | Bradley et al. |
| 5,624,803 | A | 4/1997 | Noonberg et al. |
| 5,889,136 | A | 3/1999 | Scaringe et al. |
| 6,008,400 | A | 12/1999 | Scaringe et al. |
| 2004/0005593 | A1 | 1/2004 | Lorens |
| 2004/0224405 | A1 | 11/2004 | Leake et al. |
| 2005/0048647 | A1 | 3/2005 | Taira et al. |
| 2005/0060771 | A1 | 3/2005 | Farmer et al. |
| 2007/0254842 | A1 | 11/2007 | Bankiewicz |
| 2008/0081064 | A1 | 4/2008 | Jelle et al. |
| 2009/0196903 | A1 | 8/2009 | Kliman |
| 2010/0210707 | A1 | 8/2010 | Li et al. |
| 2014/0221454 | A1* | 8/2014 | Brown ........................ 514/44 A |

OTHER PUBLICATIONS

Brummelkamp, et al. (2002) "A system for stable expression of short interfering RNAs in mammalian cells" *Science* 296(5567): 550-553.
Chen, et al. (2008) "Strand-specific 5'-O-methylation of siRNA duplexes controls guide strand selection and targeting specificity" *RNA* 14(2):263-274.
Chen, et al. (2008) "Antitumor effect of dsRNA-induced p21(WAF1/CIP1) gene activation in human bladder cancer cells" *Mol. Cancer Ther.* 7(3):698-703.
Chiu & Rana (2002) "RNAi in human cells: basic structural and functional features of small interfering RNA" *Mol. Cell* 10(3):549-561.
Core, et al. (2008) "Nascent RNA sequencing reveals widespread pausing and divergent initiation at human promoters" *Science* 322(5909):1845-1848.
Czauderna, et al. (2003) "Structural variations and stabilising modifications of synthetic siRNAs in mammalian cells" *Nucleic Acids Res* 31(11):2705-2716.
De Fougerolles, et al. (2005) "RNA interference in vivo: toward synthetic small inhibitory RNA-based therapeutics" *Methods Enzymol.* 392:278-296.
Diederichs & Haber (2007) "Dual role for argonautes in microRNA processing and posttranscriptional regulation of microRNA expression" *Cell* 131(6):1097-1108.
Elbashir, et al. (2002) "Analysis of gene function in somatic mammalian cells using small interfering RNAs" *Methods* 26(2):199-213.
Elbashir, et al. (2001) "Duplexes of 21-nucleotide RNAs mediate RNA interference in cultured mammalian cells" *Nature* 411(6836):494-498.
Faria, et al. (2001) "Phosphoramidate oligonucleotides as potent antisense molecules in cells and in vivo" *Nature Biotechnol.* 19(1):40-44.
Fire, et al. (1998) "Potent and specific genetic interference by double-stranded RNA in *Caenorhabditis elegans*" *Nature* 391(6669):806-811.
Földes-Papp, et al. (2009) "Trafficking of mature miRNA-122 into the nucleus of live liver cells" *Curr. Pharm. Biotechnol.* 10(6):569-78.
Gonzalez, et al. (2008) "Mechanistic principles of chromatin remodeling guided by siRNAs and miRNAs" *Cell Cycle* 7(16):2601-2608.
Goodrich & Kugel (2009) "From bacteria to humans, chromatin to elongation, and activation to repression: The expanding roles of noncoding RNAs in regulating transcription" *Crit. Rev. Biochem. Mol. Biol.* 44(1):3-15.
Grimm, et al. (2006) "Fatality in mice due to oversaturation of cellular microRNA/short hairpin Rna pathways" *Nature* 441(7092):537-541.
Guang, et al. (2008) "An Argonaute transports siRNAs from the cytoplasm to the nucleus" *Science* 321(5888):537-541.
Han, et al. (2007) "Promoter-associated RNA is required for RNA-directed transcriptional gene silencing in human cells" *Proc Natl Acad Sci U S A* 104(30):12422-12427.
Harborth, et al. (2001) "Identification of essential genes in cultured mammalian cells using small interfering RNAs" *J. Cell Sci.* 114(Pt. 24):4557-4565.
He, et al. (2008) "The antisense transcriptomes of human cells" *Science* 322(5909):1855-1857.
Hock & Meister (2008) "The Argonaute protein family" *Genome Biol.* 9(2):210.
Huang, et al. (2010) "RNAa is conserved in mammalian cells" *PLoS One* 5(1):e8848.
Jaenisch & Bird (2003) "Epigenetic regulation of gene expression: how the genome integrates intrinsic and environmental signals" *Nat Genet* 33 Suppl:245-254.

(Continued)

*Primary Examiner* — Amy Bowman
(74) *Attorney, Agent, or Firm* — Edward J. Baba; Shweta Chandra; Bozicevic, Field & Francis LLP

(57) ABSTRACT

Methods, compositions and kits are provided for increasing the expression of a gene product in a cell by contacting the cell with a modified small activating RNA (saRNA) molecule, which provides for an increase in gene expression that is improved over the increase in expression provided by traditional saRNAs. These methods and compositions find use in any application in which an increase in gene expression in a cell is desired.

26 Claims, 6 Drawing Sheets

(56) References Cited

OTHER PUBLICATIONS

Janowski, et al. (2007) "Activating gene expression in mammalian cells with promoter-targeted duplex RNAs" *Nat. Chem. Biol.* 3(3):166-173.

Katayama, et al. (2005) "Antisense transcription in the mammalian transcriptome" *Science* 309(5740):1564-1566.

Kawasaki & Taira (2004) "Induction of DNA methylation and gene silencing by short interfering RNAs in human cells" *Nature* 431(7005):211-217.

Khvorova, et al. (2003) "Functional siRNAs and miRNAs exhibit strand bias" *Cell* 115(2):209-216.

Kuwabara, et al. (2004) "A small modulatory dsRNA specifies the fate of adult neural stem cells" *Cell* 116(6):779-93.

Layzer, et al. (2004) "In vivo activity of nuclease-resistant siRNAs" *RNA* 10(5):766-771.

Lee, et al. (2002) "Expression of small interfering RNAs targeted against HIV-1 rev transcripts in human cells" *Nat. Biotechnol.* 20(5):500-505.

Li, L. C., et al. (2006) "Small dsRNAs induce transcriptional activation in human cells" *Proc Natl Acad Sci USA* 103(46):17337-17342.

Mahmoudi, et al. (2009) "Wrap53, a natural p53 antisense transcript required for p53 induction upon DNA damage" *Mol. Cell* 33(4):462-471.

Manoharan (2004) "RNA interference and chemically modified small interfering RNAs" *Curr. Opin. Chem. Biol.* 8(6):570-579.

Martens, et al. (2004) "Intergenic transcription is required to repress the *Saccharomyces cerevisiae* SER3 gene" Nature 429(6991):571-574.

Martinez, et al. (2002) "Single-stranded antisense siRNAs guide target RNA cleavage in RNAi" *Cell* 110(5):563-574.

Meister, et al. (2004) "Human Argonaute2 mediates RNA cleavage targeted by miRNAs and siRNAs" *Mol. Cell* 15(2):185-197.

Mette, et al. (2000) "Transcriptional silencing and promoter methylation triggered by double-stranded RNA" *EMBO J.* 19(19):5194-5201.

Miyagishi & Taira (2002) "U6 promoter-driven siRNAs with four uridine 3' overhangs efficiently suppress targeted gene expression in mammalian cells" *Nat. Biotechnol.* 20(5):497-500.

Morris, et al. (2004) "Small interfering RNA-induced transcriptional gene silencing in human cells" *Science* 305(5688):1289-1292.

Morris, et al. (2008) "Bidirectional transcription directs both transcriptional gene activation and suppression in human cells" *PLoS Genet.* 4(11):e1000258.

Paddison, et al. (2002) "Short hairpin RNAs (shRNAs) induce sequence-specific silencing in mammalian cells" *Genes Dev.* 16(8):948-958.

Paul, et al. (2002) "Effective expression of small interfering RNA in human cells" *Nat. Biotechnol.* 20(5):505-508.

Pélissier et al. (1999) "Heavy de novo methylation at symmetrical and non-symmetrical sites is a hallmark of RNA-directed DNA methylation" *Nucleic Acids Res* 27(7):1625-1634.

Petruk, et al. (2006) "Transcription of bxd noncoding RNAs promoted by trithorax represses Ubx in cis by transcriptional interference" *Cell* 127(6):1209-1221.

Place, et al. (2008) "MicroRNA-373 induces expression of genes with complementary promoter sequences" *Proc. Natl. Acad. Sci. USA* 105(5):1608-1613.

Preker, et al. (2008) "RNA exosome depletion reveals transcription upstream of active human promoters" *Science* 322(5909):1851-1854.

Provost, et al. (2002) "Ribonuclease activity and RNA binding of recombinant human Dicer" *EMBO J.* 21(21):5864-5874.

Reynolds, et al. (2004) "Rational siRNA design for RNA interference" *Nat. Biotechnol.* 22(3):326-330.

Schramke, et al. (2005) "RNA-interference-directed chromatin modification coupled to RNA polymerase II transcription" *Nature* 435(7046):1275-1279.

Schwartz, et al. (2008) "Antisense transcripts are targets for activating small RNAs" *Nat. Struct. Mol. Biol.* 15(8):842-848.

Seila, et al. (2008) "Divergent transcription from active promoters" *Science* 322(5909):1849-1851.

Sijen, et al. (2001) "Transcriptional and posttranscriptional gene silencing are mechanistically related" *Curr. Biol.* 11(6):436-440.

Sioud, et al. (2007) "Suppression of immunostimulatory siRNA-driven innate immune activation by 2'-modified RNAs" *Biochem Biophys Res Commun* 361(1):122-126.

Su, et al. (2009) "Essential and overlapping functions for mammalian Argonautes in microRNA silencing" *Genes Dev.* 23(3):304-17.

Tabara, et al. (2002) "The dsRNA binding protein RDE-4 interacts with RDE-1, DCR-1, and a DExH-box helicase to direct RNAi in *C. elegans*" *Cell* 109(7):861-871.

Takahashi, et al. (2006) "Moment analysis for kinetics of gene silencing by RNA interference" *Biotechnol. Bioeng.* 93(4):816-819.

Ting, et al. (2005) "Short double-stranded RNA induces transcriptional gene silencing in human cancer cells in the absence of DNA methylation" *Nat. Genet.* 37(8):906-910.

Toulmé (2001) "New candidates for true antisense" *Nature Biotechnol.* 19(1):17-18.

Turunen, et al. (2009) "Efficient regulation of VEGF expression by promoter-targeted lentiviral shRNAs based on epigenetic mechanism: a novel example of epigenetherapy" *Circ. Res.* 105(6):604-609.

Tuschl, (2002) "Expanding small RNA interference" *Nat. Biotechnol*, 20(5):446-448.

Volpe, et al. (2002) "Regulation of heterochromatic silencing and histone H3 lysine-9 methylation by RNAi" *Science* 297(5588):1833-1837.

Wang, et al. (2008) "Induced ncRNAs allosterically modify RNA-binding proteins in cis to inhibit nhibit transcription" *Nature* 454(7200):126-130.

Weinberg, et al. "The antisense strand of small interfering RNAs directs histone methylation and transcriptional gene silencing in human cells" (2006) *RNA* 12(2), 256-62.

Zeng, et al. (2003) "MicroRNAs and small interfering RNAs can inhibit mRNA expression by similar mechanisms" *Proc. Natl. Acad. Sci. USA* 100(17):9779-9784.

* cited by examiner

MODIFIED SMALL ACTIVATING RNA MOLECULES AND METHODS OF USE

CROSS-REFERENCE TO RELATED APPLICATIONS

This application claims the benefit of earlier-filed U.S. provisional application Ser. No. 61/329,057, filed Apr. 28, 2010, which application is incorporated herein by reference in its entirety.

GOVERNMENT RIGHTS

This invention was made with government support under grant nos. P50 CA089520, R01 GM090293 and R21 CA121774 awarded by the National Institutes of Health, and grant no. W81XWH-08-1-0260 awarded by the US Army Medical Research and Materiel Command. The government has certain rights in the invention.

BACKGROUND OF THE INVENTION

RNA interference (RNAi) is an evolutionarily conserved mechanism of gene regulation by which small double-stranded RNA (dsRNA) molecules inhibit translation or degrade complementary mRNA sequences (Elbashir, S. M., et al. (2001) Nature 411, 494-8; Fire, A., et al. (1998) Nature 391, 806-11; Zeng, Y., et al., (2003) Proc Natl Acad Sci USA 100, 9779-84.). Synthetic dsRNA duplexes, termed small interfering RNAs (siRNAs), mimic naturally processed dsRNAs [e.g. microRNAs (miRNAs)] to exploit endogenous enzymatic machinery and enter the RNAi pathway.

More recently, short dsRNAs have also been shown to induce gene expression in a phenomenon referred to as RNA activation (RNAa) (Janowski, B. A., et al. (2007) Nat Chem Biol 3, 166-73; Li, L. C., Okino, S. T., et al. (2006) Proc Natl Acad Sci USA 103, 17337-42; Place, R. F. et al. (2008) Proc Natl Acad Sci USA 105, 1608-13.). This class of dsRNA molecule—termed small activating RNAs (saRNAs) to distinguish from siRNAs—triggers an effect opposite to that of RNAi. Several models of RNAa have been described including transcriptional activation by targeting promoter-derived sequences (Li, L. C., et al. (2006) Proc Natl Acad Sci USA 103, 17337-42; Place, R. F., et al. (2008) Proc Natl Acad Sci USA 105, 1608-13; Kuwabara, T., et al. (2004) Cell 116, 779-93; Wang, X., et al. (2008) Nature 454, 126-30.) and/or gene antisense transcripts (Morris, K. V., et al. (2008) PLoS Genet 4, e1000258; Schwartz, J. C., et al. (2008) Nat Struct Mol Biol 15, 842-8.). Regardless of the target, it has become clear that RNAa has potential to induce the expression of a variety of genes. As such, RNAa offers a promising new therapeutic strategy for diseases that can be corrected by stimulating gene expression.

Identifying features of the RNAi pathway have improved its therapeutic application and development as a laboratory tool. Early studies evaluating the rate of RNAi activity defined the optimal window for target knockdown and functional gene analysis (Takahashi, Y., et al. (2006) Biotechnol Bioeng 93, 816-9; Harborth, J., et al. (2001) J Cell Sci 114, 4557-65.). Medicinal chemistry also enabled usage and identification of modifications to siRNAs that improved mechanistic analysis and pharmacological properties (Manoharan, M. (2004) Curr Opin Chem Biol 8, 570-9; de Fougerolles, A., et al. (2005) Methods Enzymol 392, 278-96; Layzer, J. M., et al. (2004) Rna 10, 766-71). Understanding the functional nuances of RNAa, and applying this understanding to the development of improved saRNAs is of equal importance. This application addresses these issues.

RELEVANT LITERATURE

U.S. Patent Application Publication No. US 2010/0210707; U.S. Patent Application Publication No. 2004/0224405; Janowski, B. A., et al. (2007) Nat Chem Biol 3, 166-73; Li, L. C., et al. (2006) Proc Natl Acad Sci USA 103, 17337-42; Place, R. F., et al. (2008) Proc Natl Acad Sci USA 105, 1608-13. Chen, Z., et al. (2008) Mol Cancer Ther 7, 698-703. Provost et al., *E.M.B.O.J.*, 1, 21(21): 5864-5874 (2002); Tabara et al., *Cell*, 109(7):861-71 (2002); Martinez et al., *Cell* 110(5):563 (2002); Mette et al *Embo J* 19:5194-201 (2000); Sijen T. et al. *Curr Biol* 11:436-40 (2001); Volpe T. A. et al. *Science* 297:1833-7 (2002); Morris et al., *Science* 305: 1289-92 (2004); Kawasaki et al., *Nature* 431:211-7 (2004); Elbashir et al., *Methods* 26:199-213 (2002); Reynolds et al., *Nat Biotechnol* 22:326-30 (2004); Pelissier et al., *Nucleic Acids Res* 27:1625-34 (1999); Ting et al., Nat Genet. 37(8): 906-10 (2005); Kawasaki et al., Nature 9:431(7005):211-7 (2004), Morris, et al. Science 305(5688):1289-92 (2004); Schramke et al., Nature 435(7046):1275-9 (2005); and Jaenisch et al., *Nat Genet* 33 Suppl:245-54 (2003).

SUMMARY OF THE INVENTION

Methods, compositions and kits are provided for increasing the expression of a gene product in a cell by contacting the cell with a modified small activating RNA (saRNA) molecule, which provides for an increase in gene expression and a decrease in off-target effects that is improved over the increase in expression provided by traditional saRNAs. These methods and compositions find use in any application in which an increase in gene expression in a cell is desired. These and other advantages of the invention will be apparent from the detailed description below.

In some aspects of the invention, an isolated composition is provided for increasing the expression of a gene product in a cell, the composition comprising a modified gene-specific small activating RNA (saRNA) comprising: i. a mismatch at the 5' terminus of the antisense strand of a gene-specific control saRNA (a gene specific control saRNA being a gene-specific saRNA not so modified); ii. a blocking moiety at the 5' terminus of the sense strand of a gene-specific control saRNA (a gene specific control saRNA being a gene-specific saRNA not so modified); or iii. a mismatch at the 5' terminus of the antisense strand and a blocking moiety at the 5' terminus of the sense strand of a gene-specific control saRNA (a gene specific control saRNA being a gene-specific saRNA not so modified). In some embodiments, the modified saRNA molecule is encoded on a nucleic acid vector. In some embodiments, the modified saRNA molecule is chemically synthesized. In some embodiments, the composition is formulated for pharmaceutical delivery.

In some embodiments, the modified gene-specific saRNA is specific for the E-cadherin gene. In some embodiments, the E-cadherin-specific control saRNA comprises a sense strand comprising the sequence SEQ ID NO:15 and an antisense strand comprising the sequence SEQ ID NO:16. In some such embodiments in which the modified E-cadherin-specific saRNA comprises a mismatch at the 5' terminus of the antisense strand, the modified saRNA comprises a sense strand comprising the sequence SEQ ID NO:31. In some such embodiments in which the modified E-cadherin-specific saRNA comprises a blocking moiety at the 5' terminus of the sense strand, the modified saRNA comprises a sense strand comprising the sequence SEQ ID NO:21. In some such embodiments in which the modified E-cadherin-specific saRNA comprises both a mismatch at the 5' terminus of the antisense strand and a block at the 5' terminus of the sense strand, the modified saRNA comprises a sense strand comprising the sequence SEQ ID NO:45.

In some embodiments, the modified gene-specific saRNA is specific for the p21 gene. In some embodiments, the p21-specific control saRNA comprises a sense strand comprising the sequence SEQ ID NO:17 and an antisense strand comprising the sequence SEQ ID NO:18. In some such embodiments in which the modified p21-specific saRNA comprises a mismatch at the 5' terminus of the antisense strand, the modified saRNA comprises a sense strand comprising the sequence SEQ ID NO:35. In some such embodiments in which the modified p21-specific saRNA comprises a blocking moiety at the 5' terminus of the sense strand, the modified saRNA comprises a sense strand comprising the sequence SEQ ID NO:25. In some such embodiments in which the modified p21-specific saRNA comprises both a mismatch at the 5' terminus of the antisense strand and a block at the 5' terminus of the sense strand, the modified saRNA comprises a sense strand comprising the sequence SEQ ID NO:47.

In some aspects of the invention, a method is provided for increasing the expression of a gene in a cell, the method comprising introducing into a cell an effective amount of a modified gene-specific small activating RNA (saRNA), the modified gene-specific saRNA comprising: i. a mismatch at the 5' terminus of the antisense strand of a gene-specific control saRNA, a control saRNA being a gene-specific saRNA not so modified; ii. a blocking moiety at the 5' terminus of the sense strand of a gene-specific control saRNA; or iii. a mismatch at the 5' terminus of the antisense strand and a block at the 5' terminus of the sense strand of a gene-specific control saRNA; wherein the expression of the gene is increased. In some embodiments, the modified saRNA molecule is introduced into the cell by expression from a nucleic acid vector. In some embodiments, the modified saRNA molecule is introduced to the cell as an RNA molecule.

In some embodiments, the modified gene-specific saRNA is specific for the E-cadherin gene. In some embodiments, the E-cadherin-specific control saRNA comprises a sense strand comprising the sequence SEQ ID NO:15 and an antisense strand comprising the sequence SEQ ID NO:16. In some such embodiments in which the modified E-cadherin-specific saRNA comprises a mismatch at the 5' terminus of the antisense strand, the modified saRNA comprises a sense strand comprising the sequence SEQ ID NO:31. In some such embodiments in which the modified E-cadherin-specific saRNA comprises a blocking moiety at the 5' terminus of the sense strand, the modified saRNA comprises a sense strand comprising the sequence SEQ ID NO:21. In some such embodiments in which the modified E-cadherin-specific saRNA comprises both a mismatch at the 5' terminus of the antisense strand and a block at the 5' terminus of the sense strand, the modified saRNA comprises a sense strand comprising the sequence SEQ ID NO:45.

In some embodiments, the modified gene-specific saRNA is specific for the p21 gene. In some embodiments, the p21-specific control saRNA comprises a sense strand comprising the sequence SEQ ID NO:17 and an antisense strand comprising the sequence SEQ ID NO:18. In some such embodiments in which the modified p21-specific saRNA comprises a mismatch at the 5' terminus of the antisense strand, the modified saRNA comprises a sense strand comprising the sequence SEQ ID NO:35. In some such embodiments in which the modified p21-specific saRNA comprises a blocking moiety at the 5' terminus of the sense strand, the modified saRNA comprises a sense strand comprising the sequence SEQ ID NO:25. In some such embodiments in which the modified p21-specific saRNA comprises both a mismatch at the 5' terminus of the antisense strand and a block at the 5' terminus of the sense strand, the modified saRNA comprises a sense strand comprising the sequence SEQ ID NO:47.

In some embodiments, the increase in gene expression following administration of the modified gene-specific saRNA is greater than the increase in expression of a gene following administration of the gene-specific control saRNA, i.e. the gene specific-saRNA not so modified. In some embodiments, the off-target, or background, effects of the modified gene-specific saRNA are less than the off-target effects following administration of the gene-specific control saRNA. In some embodiments, the increase in gene expression following administration of the modified gene-specific saRNA is greater than the increase in expression of a gene following administration of the gene-specific control saRNA, and the off-target effects of the modified gene-specific saRNA are less than the off-target effects following administration of the gene-specific control saRNAIn some aspects of the invention, a method is provided for reducing proliferation of a cell in a subject having a cellular proliferative disease, the method comprising: administering to the subject an effective amount of a modified small activating RNA (saRNA) molecule that is specific for a gene that suppresses cell proliferation, the modified small activating RNA (saRNA) comprising: i. a mismatch at the 5' terminus of the antisense strand of a control saRNA that is specific for the gene; ii. a blocking moiety at the 5' terminus of the sense strand of a control saRNA that is specific for the gene; or iii. a mismatch at the 5' terminus of the antisense strand and a block at the 5' terminus of the sense strand of a control saRNA specific for the gene, wherein the administering provides for an increase in expression of said gene, wherein cellular proliferation is decreased.

In some embodiments, the modified saRNA molecule is introduced into the cell by expression from a nucleic acid vector. In some embodiments, the modified saRNA molecule is introduced to the cell as an RNA molecule. In some embodiments, the gene is E-cadherin. In some such embodiments, the E-cadherin-specific control saRNA composition is as described above. In some such embodiments, the modified E-cadherin-specific saRNA compositions as described above. In some embodiments, the gene is p21. In some such embodiments, the p21-specific control saRNA composition is as described above. In some such embodiments, the modified p21-specific saRNA composition is as described above. In some embodiments, the increase in expression of the gene following administration of said modified saRNA is enhanced relative to the increase in expression of the gene following administration of the gene-specific control saRNA. In some embodiments, the off-target, or background, effects of the modified gene-specific saRNA are less than the off-target effects following administration of the gene-specific control saRNA. In some embodiments, the increase in gene expression following administration of the modified gene-specific saRNA is greater than the increase in expression of a gene following administration of the gene-specific control saRNA, and the off-target effects of the modified gene-specific saRNA are less than the off-target effects following administration of the gene-specific control saRNA.

In some aspects of the invention, a kit is provided comprising a modified small activating RNA (saRNA) molecule specific for the E-cadherin gene. In some aspects of the invention, a kit is provided comprising a modified small activating RNA (saRNA) molecule specific for the p21 gene.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(A-B) PC-3 cells were transfected at 50 nM dsEcad-215 (A) or dsP21-322 (B) for the indicated lengths of time in order to monitor target gene induction via RNAa. Expression levels of E-cadherin (A) and p21 (B) were assessed by standard RT-PCR. GAPDH was also evaluated and served as a loading control. (C-D) PC-3 cells were transfected at 50 nM siMOF (C) or siE2F1 (D) in order to monitor RNAi at the indicated time points. Expression levels of MOF (C) and E2F1 (D) were assessed by standard RT-PCR. (E) Expression levels of E-cadherin, p21, MOF, and E2F1 following saRNA/siRNA treatments were quantified by optical densitometry at each time point. Maximal RNAa activity (100%) correlates to E-cadherin and p21 levels at 72 hours of saRNA transfection, while maximal RNAi activity (100%) correlates to MOF and E2F1 levels at 72 hours following siRNA treatments. Target expression levels at 0 hours designated no activity (0%) for both RNAa and RNAi. Rate of gene induction or target knockdown signify RNAa (dsEcad-215 and dsP21-322) and RNAi (siMOF and siE2F1) kinetics, respectively. (F) HeLa and A498 cells were transfected with dsP21-322 at the indicted time points. Expression of p21 and GAPDH were evaluated by RT-PCR. (G-H) PC-3 cells were transfected at 50 nM dsEcad-215 (G) or siMOF (H) for the indicated lengths of time. Cells were passed prior to day 9 as denoted by an asterisk (*). Expression levels of E-cadherin (G) or MOF (H) were assessed by standard RT-PCR. GAPDH was also amplified to serve as a loading control.

Figure 2:
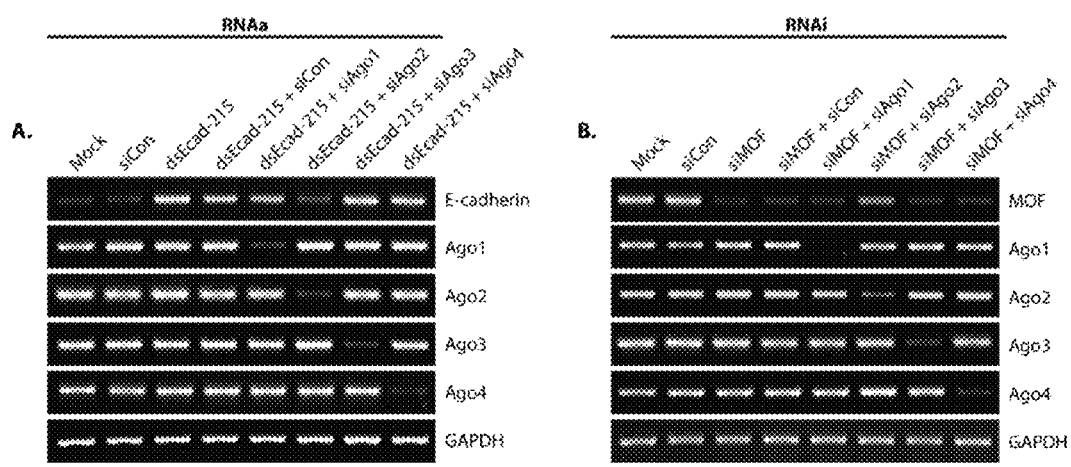

FIG. 2 depicts how knockdown of Argonaute 2 (Ago2) inhibits RNAa and RNAi function. (A) PC-3 cells were transfected at 50 nM siCon (control siRNA) or dsEcad-215 for 72 hours. Combination treatments of dsEcad-215 and Ago-specific siRNAs (siAgo1, 2, 3, or 4) were performed using 25 nM concentrations of each RNA duplex. E-cadherin, Ago1-4, and GAPDH expression levels were assessed by standard RT-PCR. GAPDH served as a loading control. (B) PC-3 cells were transfected at 50 nM siCon or siMOF for 72 hours. Co-treatments of siMOF with siAgo1-4 were performed at 25 nM each siRNA. mRNA expression levels were assessed by standard RT-PCR.

Figure 3:
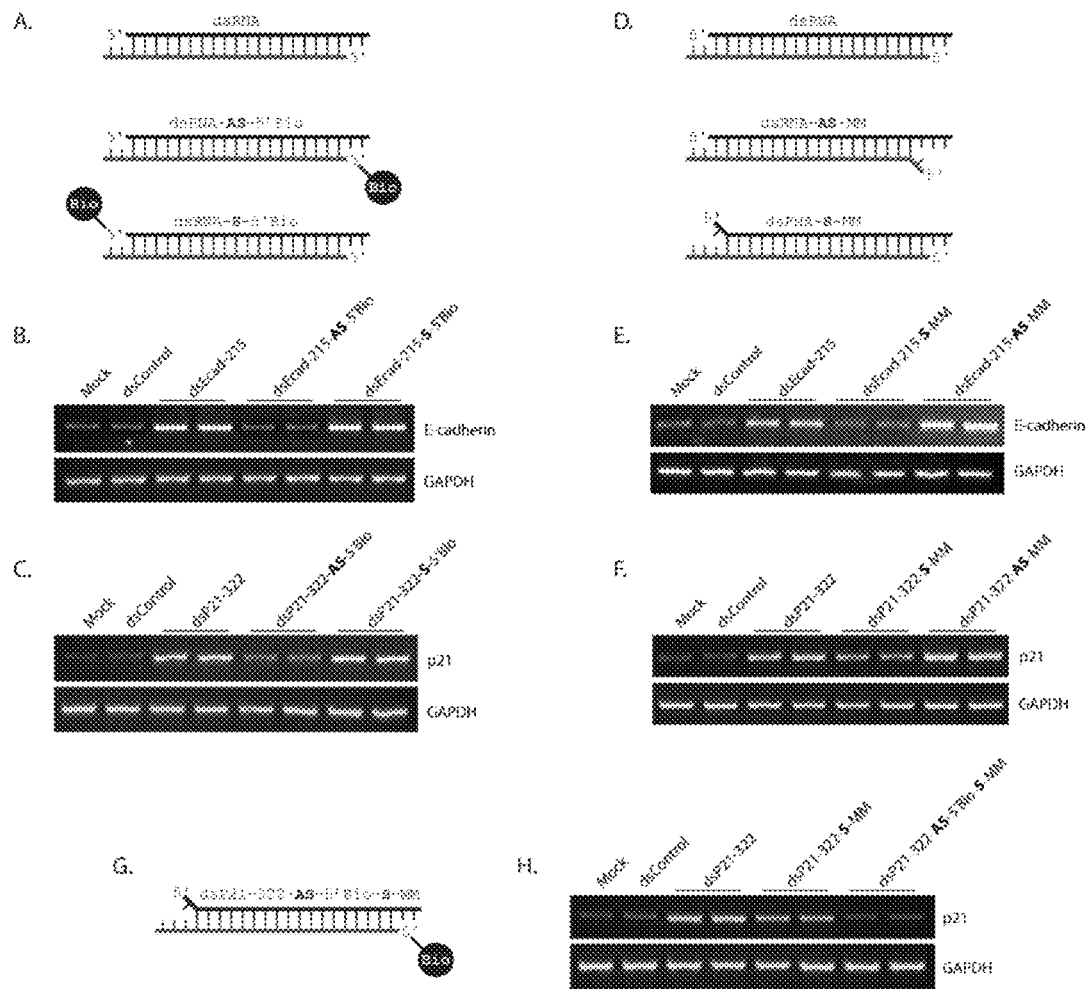

FIG. 3 illustrates strand modifications that manipulate RNAa activity and how. (A) Schematic representation of modified saRNA covalently linked to biotin at the 5'-end of the antisense (dsRNA-AS-5'Bio) or sense (dsRNA-S-5'Bio) strand. Unmodified saRNA (dsRNA) is also depicted. The antisense strand in each duplex is red, while the sense strand is in black. (B-C) PC-3 cells were transfected at 50 nM concentrations of the indicated saRNAs for 72 hours. Mock samples were transfected in the absence of saRNA. Expression levels of E-cadherin (B) or p21 (C) were assessed by standard RT-PCR. GAPDH levels were also evaluated to serve as loading controls. (D) Schematic representation of modified saRNA possessing a mismatched base opposite the 5' most nucleotide of either the antisense (dsRNA-AS-MM) or sense (dsRNA-S-MM) strand. (E-F) PC-3 cells were transfected with the indicated saRNAs for 72 hours. Expression levels of GAPDH and E-cadherin (E) or p21 (F) were assessed by standard RT-PCR. (G) Schematic depiction of dsP21-322-AS-5'Bio-S-MM. (H) PC-3 cells were transfected with the indicated saRNAs for 72 hours. Expression of p21 and GAPDH were evaluated by standard RT-PCR.

Figure 4:
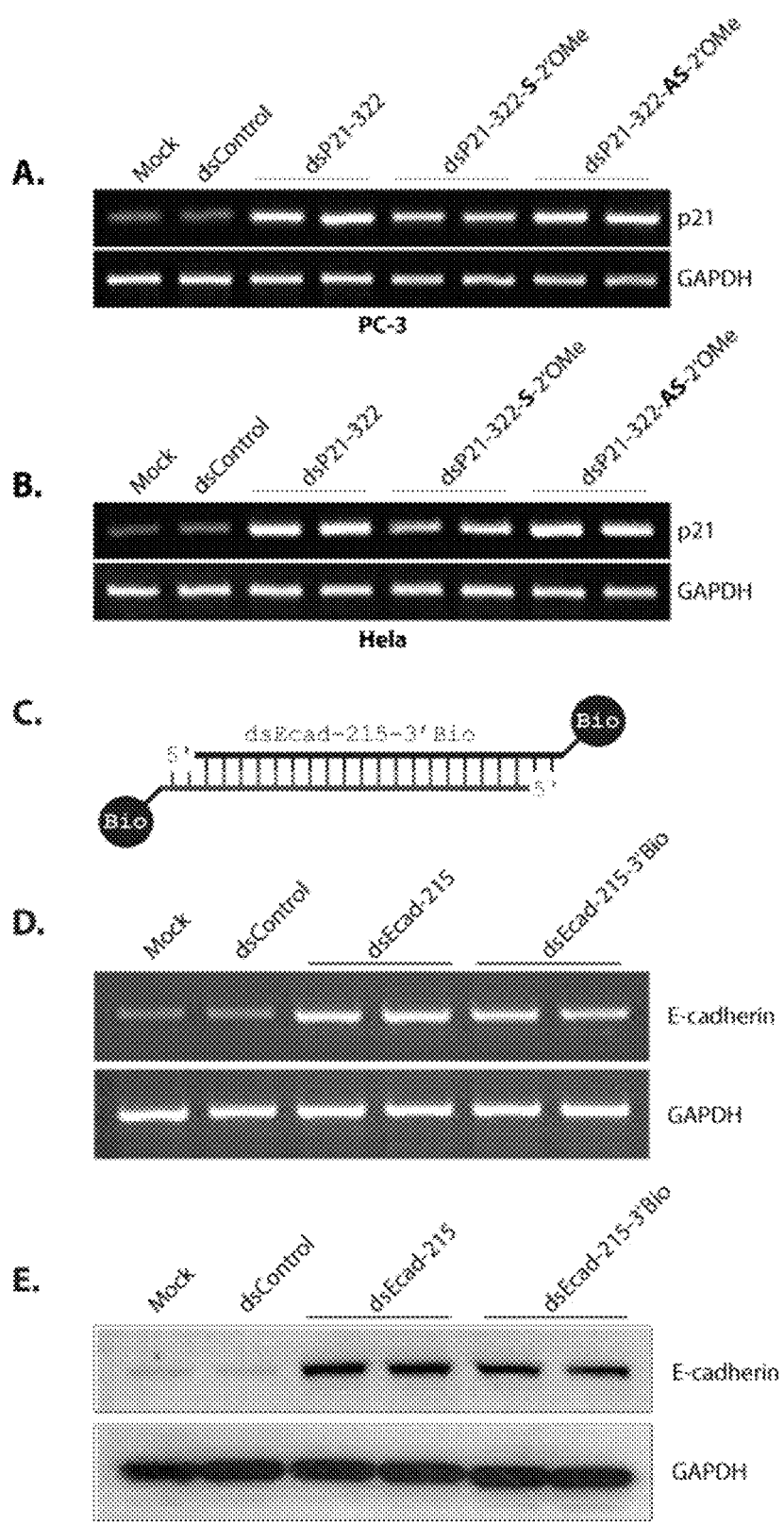

FIG. 4 depicts the effects of modifications to the 2'-sugar and 3'-termini in saRNA. (A-B) PC-3 (A) and HeLa (B) cells were transfected with 50 nM concentrations of dsControl, dsP21-322, dsP21-322-S-2'OMe, or dsP21-322-AS-2'OMe for 72 hours. Mock samples were transfected in the absence of saRNA. Expression of p21 and GAPDH were evaluated by standard RT-PCR. (C) Schematic representation of dsEcad-215-3'Bio possessing biotin covalently linked to both 3'-termini. The antisense strand is in grey, while the sense strand is black. (D) PC-3 cells were transfected at 50 nM dsControl, dsEcad-215, or dsEcad-215-3'Bio for 72 hours. Expression of E-cadherin and GAPDH mRNA levels were evaluated by standard RT-PCR. (E) Induction of E-cadherin protein was confirmed by immunoblot analysis. GAPDH was also detected and served as a loading control.

Figure 5:
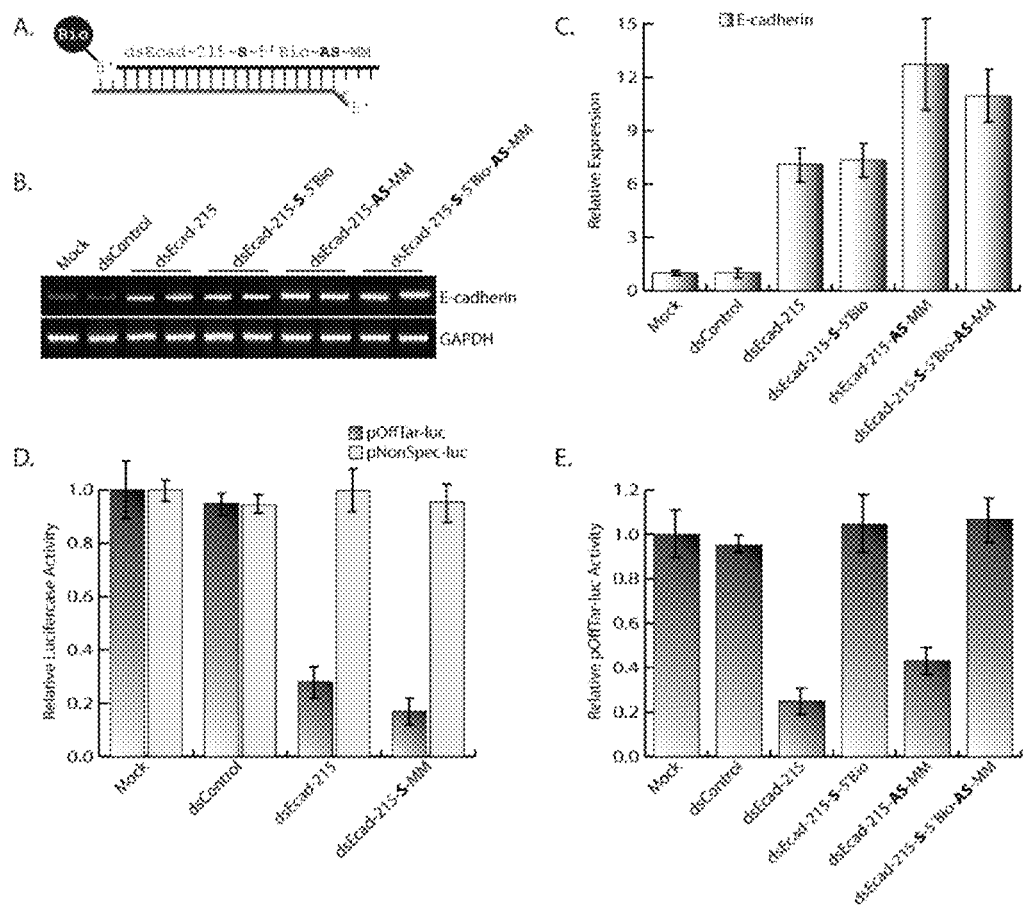

FIG. 5 illustrates how strand modifications may be utilized to improve RNAa function. (A) Depiction of dsEcad-215-S-5'Bio-AS-MM possessing biotin covalently linked to the 5'-terminus of the sense strand and a mismatched base opposite the 5' most nucleotide of the antisense strand. The antisense strand is in grey, while the sense strand is black. (B) PC-3 cells were transfected with 50 nM concentrations of the indicated E-cadherin saRNAs for 72 hours. Expression levels of E-cadherin and GAPDH were assessed by standard RT-PCR. GAPDH served as a loading control. (C) Relative expression of E-cadherin was determined by real-time PCR (mean±standard error from three independent experiments). Values of E-cadherin were normalized to GAPDH. The level of E-cadherin induction signifies the RNAa activity generated by each saRNA molecule. (D) Relative luciferase activity of pOffTar-luc or pNonSpec-luc in PC-3 cells transfected with mock, dsControl, dsEcad-215, or dsEcad-215-S-MM. Treatment with dsEcad-215-S-MM served as a positive control for targeted reduction of pOffTar-luc activity. (E) Luciferase activity of pOffTar-luc in PC-3 cells transfected with the indicated saRNA molecules. Off-target activity was validated by a reduction in pOffTar-luc luciferase activity.

Figure 6:
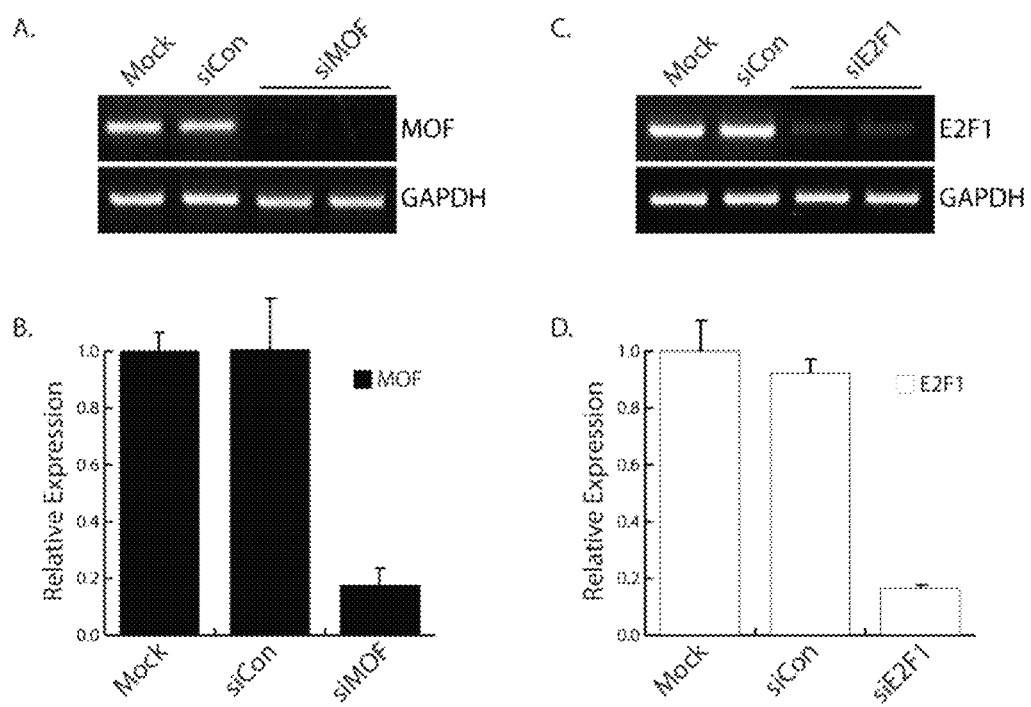

FIG. 6 demonstrates efficient knockdown of MOF and E2F1 by RNAi. (A) PC-3 cells were transfected at 50 nM siCon or siMOF for 72 hours. Mock treatments were transfected in the absence of siRNA. MOF and GAPDH mRNA levels were assessed by standard RT-PCR. GAPDH served as a loading control. (B) Relative expression of MOF was determined by real-time PCR (mean±standard error from three independent experiments). Values of MOF were normalized to GAPDH. (C) PC-3 cells were transfected at 50 nM siCon or siE2F1 for 72 hours. E2F1 and GAPDH transcript levels were assessed by standard RT-PCR. (D) Relative expression of E2F1 was determined by real-time PCR (mean±standard error from three independent experiments).

DETAILED DESCRIPTION OF THE INVENTION

Methods and compositions are provided for increasing the expression of a gene product in a cell by contacting the cell with a modified small activating RNA (saRNA) molecule, which provides for an increase in gene expression that is greater than the increase in expression provided by traditional saRNAs. Also provided are kits for practicing the subject methods of the invention. These methods, compositions and kits find use in any application in which an increase in gene expression in a cell is desired. These and other advantages of the invention will be apparent from the detailed description below.

Before the present invention described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a sample" includes a plurality of such samples and reference to "the molecule" includes reference to one or more molecules and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

As used herein the term "isolated" is meant to describe a compound of interest (e.g., either a polynucleotide or a polypeptide) that is in an environment different from that in which the compound might naturally occur.

"Purified" as used herein refers to a compound removed from an environment in which it was produced and is at least 60% free, preferably 75% free, and most preferably 90% free from other components with which it is naturally associated or with which it was otherwise associated with during production.

The terms "small activating RNA" or "saRNA" refers to a ribonucleotide-based molecule comprising a first ribonucleic acid strand comprising a ribonucleotide sequence complementary to a non-coding nucleic acid sequence of the gene, wherein this region of complementarity is selected so as to provide for an increase in transcription of the corresponding gene, and usually at least two terminal residues at the 3' end which are not complementary to the non-coding sequence (e.g., dTdT). The region of complementarity is usually more than about 14 residues and less than 30, usually less than 26 nucleotides. The saRNA can be provided as a two-stranded molecule, with a second strand complementary to the first strand and forming a duplex region with the first strand, usually with at least a two residue overhang at the 3' ends of each of the first and second strands. The saRNA can also be provided as a single stranded molecule that forms a duplex region, wherein the first region comprises a ribonucleotide sequence complementary to a non-coding nucleic acid sequence of the gene, and a second region comprises a ribonucleotide sequence complementary to the first region and forming a duplex with the first region, usually with at least a two residue overhang at the 3' ends of the strand. Where the saRNA is provided as a single stranded molecule, the first region is colloquially considered "a first strand", and the second region is considered a "second strand."

The term "antisense strand" refers to the ribonucleotide sequence of an RNA molecule that is complementary to a target nucleic acid sequence of a gene, e.g. the first strand of an saRNA as described above.

The term "sense strand" refers to the ribonucleotide sequence of an RNA molecule that is complementary to an antisense strand, e.g. the second strand of an saRNA as described above.

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes."

Perfect complementarity or 100% complementarity refers to the situation in which each nucleotide unit of one polynucleotide strand can hydrogen bond with a nucleotide unit of a second polynucleotide strand, without a "mismatch". Less than perfect complementarity refers to the situation in which not all nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. Substantial complementarity refers to about 79%, about 80%, about 85%, about 90%, about 95%, or greater complementarity. Thus, for example, two polynucleotides of 29 nucleotide units each, wherein each comprises a di-dT at the 3' terminus such that the duplex region spans 27 bases, and wherein 26 of the 27 bases of the duplex region on each strand are complementary, are substantially complementary since they are 96.3% complementary when excluding the di-dT overhangs. In determining complementarity, overhang regions are excluded.

The term "conjugate" refers to a polynucleotide that is covalently or non-covalently associated with a molecule or moiety that alters the physical properties of the polynucleotide such as increasing stability of dsRNA, facilitating cellular uptake of double stranded RNA by itself, or modulating the activity of double stranded RNA in the cell. A "terminal conjugate" may have a molecule or moiety attached directly or indirectly through a linker to a 3' and/or 5' end of a polynucleotide or double stranded polynucleotide. An internal conjugate may have a molecule or moiety attached directly or indirectly through a linker to a base, to the 2' position of the ribose, or to other positions that do not interfere with Watson-Crick base pairing, for example, 5-aminoallyl uridine. In a double stranded polynucleotide, one or both 5' ends of the strands of polynucleotides comprising the double stranded polynucleotide can bear a conjugated molecule or moiety, and/or one or both 3' ends of the strands of polynucleotides comprising the double stranded polynucleotide can bear a conjugated molecule or moiety.

Conjugates may contain, for example, amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of conjugates are steroids, such as cholesterol, phospholipids, di- and tri-acylglycerols, fatty acids, hydrocarbons that may or may not contain unsaturation or substitutions, enzyme substrates, biotin, digoxigenin, and polysaccharides. Still other examples include thioethers such as hexyl-S-tritylthiol, thiocholesterol, acyl chains such as dodecandiol or undecyl groups, phospholipids such as di-hexadecyl-rac-glycerol, triethylammonium 1,2-di-O-hexadecyl-rac-glycer-o-3-H-phosphonate, polyamines, polyethylene glycol, adamantane acetic acid, palmityl moieties, octadecylamine moieties, hexylaminocarbonyl-oxyc-holesterol, farnesyl, geranyl and geranylgeranyl moieties. Conjugates can also comprise a detectable label. For example, conjugates can be a polynucleotide covalently attached to a fluorophore. Conjugates may include fluorophores such as TAMRA, BODIPY, Cyanine derivatives such as Cy3 or Cy5, Dabsyl, or any other suitable fluorophore known in the art.

A conjugate molecule or moiety may be attached to any position on the terminal nucleotide that is convenient and that does not substantially interfere with the desired activity of the polynucleotide(s) that bear it, for example the 3' or 5' position of a ribosyl sugar. A conjugate molecule or moiety substantially interferes with the desired activity of an saRNA if it adversely affects its functionality such that the ability of the saRNA to promote gene transcription is reduced by greater than 80% in an in vitro assay employing cultured cells, where the functionality is measured at 48 hours post transfection.

A "blocking conjugate" or "blocking moiety" is a conjugate molecule or moiety that is conjugated to a polynucleotide strand of a saRNA for the purposes of substantially interfering with the activity from that polynucleotide strand. For example, in instances in which it is desirable to enhance or augment the increase in gene expression observed by administration of a traditional saRNA, a blocking moiety may be conjugated is the sense strand of the saRNA. A blocking moiety substantially interferes with the activity of the polynucleotide strand to which it is conjugated if it affects its functionality such that the ability of the saRNA to promote gene transcription from that strand is reduced by greater than 50% in an in vitro assay employing cultured cells, where the functionality is measured at 48 hours post transfection. Blocking moieties are usually bulky moieties, e.g. a biotin moiety, an antibody, a polymer, or other protein or chemical compound, although smaller moieties may also be used as blocking moieties. Blocking moieties are usually conjugated to the 5' terminal region, more usually the 5' terminal nucleotide of the polynucleotide strand to be blocked.

The phrase or "effective concentration" refers to a concentration of saRNA in a cell effective to cause an increase in transcription of a gene of interest in the cell. Of particular interest is an effective concentration that provides a greater than or equal to at least about 45% or more increase, including about 50% or more, about 60% or more, about 70% or more, about 75% or more, about 80% or more increase in target sequence activity relative to a basal expression level, at levels of about 10 nM at 24, 48, 72, and 96 hours following administration, with concentrations of saRNA that provide for a greater than or equal to at least about 25% or more increase, including about 30% or more, about 35% or more, about 40% increase of target sequence activity at about 10 nM at 48 hours following administration also being considered effective, although of less interest. Target sequence activity may be measured by any method known in the art. For example, where the target sequence is a promoter, target sequence activity may be measured by level of transcription, level of the RNA whose transcription is operably linked or operably associated with the promoter, level of the protein whose transcription is operably linked or operably associated with the promoter, or activity of the protein whose transcription is operably linked or operably associated with the promoter.

The term "polynucleotide" refers to polymers of nucleotides, and includes but is not limited to single stranded or double stranded molecule of DNA, RNA, or DNA/RNA hybrids including polynucleotide chains of regularly and irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides wherein the substitution or attachment of various entities or moieties to the nucleotide units at any position, as well as naturally-occurring or non-naturally occurring backbones, are included.

The term "polyribonucleotide" refers to a polynucleotide comprising two or more modified or unmodified ribonucleotides and/or their analogs.

The term "ribonucleotide" and the phrase "ribonucleic acid" (RNA), refer to a naturally occurring or non-naturally occurring (artificial, synthetic), modified or unmodified nucleotide or polynucleotide. A ribonucleotide unit comprises an oxygen attached to the 2' position of a ribosyl moiety that has a nitrogenous base attached in N-glycosidic linkage at the 1' position of a ribosyl moiety, and a moiety that either allows for linkage to another nucleotide or precludes linkage. "Ribonucleic acid" as used herein can have a naturally occurring or modified phosphate backbone (e.g., as produced by synthetic techniques), and can include naturally-occurring or non-naturally-occurring, genetically encodable or non-genetically encodable, residues.

The term "deoxyribonucleotide" refers to a nucleotide or polynucleotide lacking an OH group at the 2' and/or 3' position of a sugar moiety. Instead it has a hydrogen bonded to the 2' and/or 3' carbon. Within an saRNA molecule that comprises one or more deoxyribonucleotides, "deoxyribonucleotide" refers to the lack of an OH group at the 2' position of the sugar moiety, having instead a hydrogen bonded directly to the 2' carbon. "Deoxyribonucleic acid" as used herein can have a naturally occurring or modified phosphate backbone (e.g., as produced by synthetic techniques), and can include naturally-occurring or non-naturally-occurring, genetically encodable or non-genetically encodable, residues.

The term "gene" as used herein includes sequences of nucleic acids that when present in an appropriate host cell facilitates production of a gene product. "Genes" can include nucleic acid sequences that encode proteins, and sequences that do not encode proteins, and includes genes that are endogenous to a host cell or are completely or partially recombinant (e.g., due to introduction of a exogenous polynucleotide encoding a promoter and a coding sequence, or introduction of a heterologous promoter adjacent an endogenous coding sequence, into a host cell). For example, the term "gene" includes nucleic acid that can be composed of exons and introns. Sequences that code for proteins are, for example, sequences that are contained within exons in an open reading frame between a start codon and a stop codon., "Gene" as used herein can refer to a nucleic acid that includes, for example, regulatory sequences such as promoters, enhancers and all other sequences known in the art that control the transcription, expression, or activity of another gene, whether the other gene comprises coding sequences or non-coding sequences. In one context, for example, "gene" may be used to describe a functional nucleic acid comprising regulatory sequences such as promoter or enhancer. The expression of a recombinant gene may be controlled by one or more heterologous regulatory sequences. "Heterologous" refers to two elements that are not normally associated in nature.

The phrase "non-coding sequence", as in "non-coding target sequence" or "non-coding nucleic acid sequence" refers to a nucleic acid sequence of interest that is not contained within an exon or is a regulatory sequence, e.g. a sequence within a promoter, enhancer, intron, etc.

The term "target sequence" is used herein to refer to a sequence within a gene to which a saRNA is directed and to which the saRNA specifically and selectively binds for the purpose of effectuating an enhancement of expression of that gene. A target sequence typically has some degree of complementarity to the anti-sense strand of the saRNA. A target sequence may be endogenous to the gene, i.e. naturally occurring in the gene, or may be ectopic to the gene, i.e. engineered to be in functional association with the gene.

The term "off-target effects" or "background" is used herein to refer to the increase in transcription, translation or expression or activity of a nucleic acid following administration of target sequence-specific saRNA that does not comprise the target sequence of the saRNA.

A "target gene" is a gene containing a target sequence to which a saRNA is directed for the purpose of effectuating an enhancement of expression. Either or both "gene" and "target gene" may be nucleic acid sequences naturally occurring in an organism, transgenes, viral or bacterial sequences, chromosomal or extrachromosomal, and/or transiently or chronically transfected or incorporated into the cell and/or its chromatin. A "target gene" can, upon saRNA-mediated activation, repress the activity of another "gene" such as a gene coding for a protein (as measured by transcription, translation, expression, or presence or activity of the gene's protein product). In another example, a "target gene" can comprise an enhancer, and saRNA mediated activation of the enhancer may increase the functionality of an operably linked or operably associated promoter, and thus increase the activity of another "gene" such as a gene coding for a protein that is operably linked to the increased promoter and/or enhancer.

A "gene-specific saRNA" is an saRNA that selectively modulates the transcription of a target gene, i.e. a gene associated with a target sequence to which the saRNA is directed.

"Regulatory elements" are nucleic acid sequences that regulate, induce, repress, or otherwise mediate the transcription, translation of a protein or RNA coded by a nucleic acid sequence with which they are operably linked or operably associated. Typically, a regulatory element or sequence such as, for example, an enhancer or repressor sequence, is operatively linked or operatively associated with a protein or RNA coding nucleic acid sequence if the regulatory element or regulatory sequence mediates the level of transcription, translation or expression of the protein coding nucleic acid sequence in response to the presence or absence of one or more regulatory factors that control transcription, translation and/or expression. Regulatory factors include, for example, transcription factors. Regulatory sequences may be found in introns.

Regulatory sequences or element include, for example, "TATAA" boxes, "CAAT" boxes, differentiation-specific elements, cAMP binding protein response elements, sterol regulatory elements, serum response elements, glucocorticoid response elements, transcription factor binding elements such as, for example, SPI binding elements, and the like. A "CAAT" box is typically located upstream (in the 5' direction) from the start codon of a eukaryotic nucleic acid sequence encoding a protein or RNA. Examples of other regulatory sequences include splicing signals, polyadenylation signals, termination signals, and the like. Further examples of nucleic acid sequences that comprise regulatory sequences include the long terminal repeats of the Rous sarcoma virus and other retroviruses. An example of a regulatory sequence that controls tissue-specific transcription is the interferon-epsilon regulatory sequence that preferentially induces production of the operably linked sequence encoding the protein in placental, tracheal, and uterine tissues, as opposed to lung, brain, liver, kidney, spleen, thymus, prostate, testis, ovary, small intestine, and pancreatic tissues. Many, many regulatory sequences are known in the art, and the foregoing is merely illustrative of a few.

The term "enhancer" and phrase "enhancer sequence" refer to a variety of regulatory sequence that can increase the efficiency of transcription, without regard to the orientation of the enhancer sequence or its distance or position in space from the promoter, transcription start site, or first codon of the nucleic acid sequence encoding a protein with which the enhancer is operably linked or associated.

The term "promoter" refers to a nucleic acid sequence that does not code for a protein, and that is operably linked or operably associated to a protein coding or RNA coding nucleic acid sequence such that the transcription of the operably linked or operably associated protein coding or RNA coding nucleic acid sequence is controlled by the promoter. Typically, eukaryotic promoters comprise between 100 and 5,000 base pairs, although this length range is not meant to be limiting with respect to the term "promoter" as used herein. Although typically found 5' to the protein coding nucleic acid sequence to which they are operably linked or operably associated, promoters can be found in intron sequences as well.

The term "promoter" is meant to include regulatory sequences operably linked or operably associated with the same protein or RNA encoding sequence that is operably linked or operably associated with the promoter. Promoters can comprise many elements, including regulatory elements. The term "promoter" comprises promoters that are inducible, wherein the transcription of the operably linked nucleic acid sequence encoding the protein is increased in response to an inducing agent. The term "promoter" may also comprise promoters that are constitutive, or not regulated by an inducing agent.

The phrases "operably associated" and "operably linked" refer to functionally related nucleic acid sequences. By way of example, a regulatory sequence is operably linked or operably associated with a protein encoding nucleic acid sequence if the regulatory sequence can exert an effect on the expression of the encoded protein. In another example, a promoter is operably linked or operably associated with a protein encoding nucleic acid sequence if the promoter controls the transcription of the encoded protein. While operably associated or operably linked nucleic acid sequences can be contiguous with the nucleic acid sequence that they control, the phrases "operably associated" and "operably linked" are not meant to be limited to those situations in which the regulatory sequences are contiguous with the nucleic acid sequences they control.

The term "nucleotide" refers to a ribonucleotide or a deoxyribonucleotide or an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs.

"Nucleotide analogs" include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety as defined herein. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

"Modified bases" refer to nucleotide bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine. The term "nucleotide" is also meant to include the N3' to P5' phosphoramidate, resulting from the substitution of a ribosyl 3' oxygen with an amine group.

Further, the term "nucleotide" also includes those species that have a detectable label, such as for example a radioactive or fluorescent moiety, or mass label attached to the nucleotide.

The phrase "nucleotide unit" refers to a single nucleotide residue and is comprised of a modified or unmodified nitrogenous base, a modified or unmodified sugar, and a modified or unmodified moiety that allows for linking of two nucleotides together or a nucleotide to a conjugate that precludes further linkage. The single nucleotide residue may be in a polynucleotide. Thus, a polynucleotide having 27 bases has 27 nucleotide units.

The phrase "nuclear uptake enhancing modification" refers to a modification of a naturally occurring or non-naturally occurring polynucleotide that provides for enhanced nuclear uptake. An example of a "nuclear uptake enhancing modification" is a stabilizing modification, such as a modified internucleotide linkage, that confers sufficient stability on a molecule, such as a nucleic acid, to render it sufficiently resistant to degradation (e.g., by nucleases) such that the associated nucleic acid can accumulate in the nucleus of a cell when exogenously introduced into the cell. In this example, entry into the cell's nucleus is facilitated by the ability of the modified nucleic acid to resist nucleases sufficiently well such that an effective concentration of the nucleic acid can be achieved inside the nucleus. An effective concentration is a concentration that results in a detectable change in the transcription or activity of a gene or target sequence as the result of the accumulation of nucleic acid within the nucleus.

The phrases "orthoester protected" and "orthoester modified" refer to modification of a sugar moiety within a nucleotide unit with an orthoester. Preferably, the sugar moiety is a ribosyl moiety. In general, orthoesters have the structure $RC(OR')_3$ wherein each R' can be the same or different, R can be an H, and wherein the underscored C is the central carbon of the orthoester. The orthoesters of the present invention are comprised of orthoesters wherein a carbon of a sugar moiety in a nucleotide unit is bonded to an oxygen, which is in turn bonded to the central carbon of the orthoester. To the central carbon of the orthoester is, in turn, bonded two oxygens, such that in total three oxygens bond to the central carbon of the orthoester. These two oxygens bonded to the central carbon (neither of which is bonded to the carbon of the sugar moiety) in turn, bond to carbon atoms that comprise two moieties that can be the same or different. For example, one of the oxygens can be bound to an ethyl moiety, and the other to an isopropyl moiety. In one example, R can be an H, one R' can be a ribosyl moiety, and the other two R' moieties can be 2-ethyl-hydroxyl moieties. Orthoesters can be placed at any position on the sugar moiety, such as, for example, on the 2', 3' and/or 5' positions. Exemplary orthoesters, and methods of making orthoester protected polynucleotides, are described in U.S. Pat. Nos. 5,889,136 and 6,008,400, each herein incorporated by reference in its entirety.

The term "stabilized" refers to the ability of a dsRNA to resist degradation while maintaining functionality and can be measured in terms of its half-life in the presence of, for example, biological materials such as serum. The half-life of an saRNA or an siRNA in, for example, serum refers to the time taken for the 50% of saRNA or siRNA to be degraded.

The phrase "duplex region" refers to the region in two complementary or substantially complementary polynucleotides that form base pairs with one another, either by Watson-Crick base pairing or any other manner that allows for a duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity generally refers to about at least 79%, about 80%, about 85%, about 85%, about 90%, about 95% or greater complementarity. For example, a mismatch in a duplex region consisting of 19 base pairs (i.e., 18 base pairs and one mismatch) results in about 94.7% complementarity, rendering the duplex region substantially complementary. In another example, three mismatches in a duplex region consisting of 19 base pairs (i.e., 16 base pairs and three mismatches) results in about 84.2% complementarity, rendering the duplex region substantially complementary, and so on.

The term "overhang" refers to a terminal (5' or 3') non-base pairing nucleotide resulting from one strand extending beyond the other strand within a doubled stranded polynucleotide. One or both of two polynucleotides that are capable of forming a duplex through hydrogen bonding of base pairs may have a 5' and/or 3' end that extends beyond the 3' and/or 5' end of complementarity shared by the two polynucleotides. The single-stranded region extending beyond the 3' and/or 5' end of the duplex is referred to as an overhang.

The term "mismatch" refers to a non-base pairing nucleotide between two nucleotides on opposite strands of a double stranded polynucleotide. One of two polynucleotides that are capable of forming a duplex through hydrogen bonding of base pairs will comprise a nucleotide that does not hydrogen bond with the nucleotide at the position in the opposite strand.

The phrase "gene silencing" refers to the reduction in transcription, translation or expression or activity of a nucleic acid, as measured by transcription level, mRNA level, enzymatic activity, methylation state, chromatin state or configuration, translational level, or other measure of its activity or state in a cell or biological system. Such activities or states can be assayed directly or indirectly. "Gene silencing" refers to the reduction or amelioration of activity associated with a nucleic acid sequence, such as its ability to function as a regulatory sequence, its ability to be transcribed, its ability to be translated and result in expression of a protein, regardless of the mechanism whereby such silencing occurs.

As used herein, the terms "gene activating", "activating a gene", and "gene activation", are interchangeable and refer to an increase in transcription, translation or expression or activity of a nucleic acid, as measured by transcription level, mRNA level, enzymatic activity, methylation state, chromatin state or configuration, translational level, or other measure of its activity or state in a cell or biological system. Such activities or states can be assayed directly or indirectly. Furthermore, "gene activating", "activating a gene", or "gene activation" refer to the increase of activity associated with a nucleic acid sequence, such as its ability to function as a regulatory sequence, its ability to be transcribed, its ability to be translated and result in expression of a protein, regardless of the mechanism whereby such activation occurs.

As used herein, the terms "increasing the expression of a gene", "increasing gene expression", "promoting the expression of a gene", or "promoting gene expression" are interchangeable and refer to an increase in the expression of a gene in a cell or biological system. This increase may be from undetectable levels, i.e. no expression or expression that is so low as to be undetectable, to levels that are detectable; or from one detectable level to a higher detectable level. Levels may be detected by any convenient method in the art for measuring transcription level, mRNA level, enzymatic activity, methylation state, chromatin state or configuration, translational level, or other measure of its activity or state in a cell or biological system.

By "enhanced efficiency of gene activation" it is meant that a composition demonstrates an enhanced ability to promote/increase gene expression in a cell relative to a control composition. Compositions of the invention that demonstrate an enhanced efficiency of gene activation have the ability to promote/increase the expression of a target gene that is at least 125% of the ability of a control compositions, i.e. about 125%, about 150%, about 200%, about 300%, about 400% or more of the ability of the control compositions. In other words, the subject composition enhances or augments the increase in gene expression observed with the control composition by about 1.25-fold, about 1.5-fold, about 2-fold, about 3-fold, about 4-fold, or more. This enhancement may be realized as an increase in the level of gene expression, i.e. the amount of gene transcript made; as a decrease in the rate of induction, i.e. the length of time that elapses between when the cell is contacted with the saRNA and when an increase in gene expression is observed; and/or as an increase in the duration of gene activation, that is, the length of time over which increased gene expression is observed.

The phrase "RNA interference" and the term "RNAi" refer to the process by which a polynucleotide or double stranded polynucleotide comprising at least one ribonucleotide unit exerts an effect on a biological process through disruption of gene expression. The process includes but is not limited to gene silencing by degrading mRNA, interactions with tRNA, rRNA, hnRNA, cDNA and genomic DNA, as well as methylation of DNA and ancillary proteins.

The term "siRNA" and the phrase "short interfering RNA" refer to a double stranded nucleic acid that is capable of performing RNAi and that is between 18 and 30 base pairs in length (i.e., a duplex region of between 18 and 30 base pairs). Additionally, the term siRNA and the phrase "short interfering RNA" include nucleic acids that also contain moieties other than ribonucleotide moieties, including, but not limited to, modified nucleotides, modified internucleotide linkages, non-nucleotides, deoxynucleotides and analogs of the aforementioned nucleotides. In contrast, the saRNAs of the invention are distinct from, and thus are not, siRNAs. saRNAs do not facilitate RNAi or gene silencing.

siRNAs can be duplexes, and can also comprise short hairpin RNAs, RNAs with loops as long as, for example, 4 to 23 or more nucleotides, RNAs with stem loop bulges, microRNAs, and short temporal RNAs. RNAs having loops or hairpin loops can include structures where the loops are connected to the stem by linkers such as flexible linkers. Flexible linkers can be comprised of a wide variety of chemical structures, as long as they are of sufficient length and materials to enable effective intramolecular hybridization of the stem elements. Typically, the length to be spanned is at least about 10-24 atoms.

The term "histone" refers to a type of protein that is found in the nucleus of eukaryotic cells. The class of proteins referred to as histones are those proteins around which DNA coils in order to compact itself.

The phrase "mammalian cell" refers to a cell of any mammal, including humans. The phrase refers to cells in vivo, such as, for example, in an organism or in an organ of an organism. The phrase also refers to cells in vitro, such as, for example, cells maintained in cell culture.

The term "methylation" refers to the attachment of a methyl group (—CH$_3$) to another molecule. Typically, when DNA undergoes methylation, a methyl group is added to a cytosine bearing nucleotide, commonly at a CpG sequence, although methylation can occur at other sites as well. Proteins, such as, for example, histone 3, may also be methylated at a lysine, e.g., lysine 9.

The term "demethylation" refers to the removal of a methyl group (—CH$_3$) from another molecule. Typically, when DNA undergoes demethylation, a methyl group is removed from a cytosine bearing nucleotide, commonly at a CpG sequence, although demethylation can occur at other sites as well. Proteins, such as, for example, histone 3, may also be demethylated at a lysine, e.g., lysine 9.

The phrase "pharmaceutically acceptable carrier" refers to compositions that facilitate the introduction of dsRNA into a cell and includes but is not limited to solvents or dispersants, coatings, anti-infective agents, isotonic agents, agents that mediate absorption time or release of the inventive polynucleotides and double stranded polynucleotides. Examples of "pharmaceutically acceptable carriers" include liposomes that can be neutral or cationic, can also comprise molecules such as chloroquine and 1,2-dioleoyl-sn-glycero-3-phosphatidyle-thanolamine, which can help destabilize endosomes and thereby aid in delivery of liposome contents into a cell, including a cell's nucleus. Examples of other pharmaceutically acceptable carriers include poly-L-lysine, poly-alkylcyanoacrylate nanoparticles, polyethyleneimines, and any suitable PAMAM dendrimers (polyamidoamine) known in the art with various cores such as, for example, ethylenediamine cores, and various surface functional groups such as, for example, cationic and anionic functional groups, amines, ethanolamines, aminodecyl.

Overview

The present invention provides methods, compositions and kits for increasing the expression of a gene by introducing in the nucleus of a cell at least one modified small activating RNA (saRNA) molecule. As described above, an saRNA is a ribonucleotide-based molecule comprising a first ribonucleic acid strand comprising a ribonucleotide sequence complementary to a non-coding nucleic acid sequence of the gene, wherein this region of complementarity is selected so as to provide for an increase in transcription of the corresponding gene, and usually at least two terminal residues at the 3' end which are not complementary to the non-coding sequence (e.g., dTdT). The region of complementarity is usually more than about 14 residues and less than 30, usually less than 26 nucleotides. The saRNA can be provided as a two-stranded molecule, with a second strand complementary to the first strand and forming a duplex region with the first strand. The saRNA can also be provided as a single stranded molecule that forms a duplex region, wherein the first region comprises a ribonucleotide sequence complementary to a non-coding nucleic acid sequence of the gene, and a second region comprises a ribonucleotide sequence complementary to the first region and forming a duplex with the first region. As known in the art, that administration of a gene-specific saRNA to a cell increases the expression of the target gene within that cell. See, for example, U.S. Patent Application Publication No. US 2010/0210707, the entire disclosure of which is incorporated here by reference.

This invention is based in part on the surprising discovery that a gene-specific saRNA that is modified to include a mismatch at the 5' terminal region of the antisense strand and/or a blocking moiety at the 5' terminal region of the sense strand of the saRNA will effect an increase in expression of the target gene that is greater than the increase in expression that would be effected in the absence of such modifications, and a decrease in the off-target, or background effects that would occur in the absence of such modifications. In other words, not only is an increase in expression observed, but the increase in expression is enhanced relative to the increase in expression of a gene following administration of a gene-specific control saRNA that is not modified to comprise a mismatch at the 5' terminal region of the antisense strand or a blocking moiety at the 5' terminal region of the sense strand. Without wishing to be bound by theory, it is believed that the incorporation of a mismatch into the 5' terminal region of the antisense strand enhances the activation of gene expression by the modified saRNA by promoting the use of the antisense strand over the sense strand by the saRNA machinery, which both increases activity from the antisense strand and decreases the activity—and hence off-target effects—from the sense strand. Similarly, the incorporation of a blocking moiety into the 5' terminal region of the sense strand enhances the activation of gene expression by the modified saRNA by promoting the use of the antisense strand over the sense strand by the saRNA machinery, which again both increases activity from the antisense strand and decreases the off-target effects due to activity from the sense strand.

One aspect the invention provides a modified gene-specific saRNA molecule, wherein the modified saRNA molecule has a first strand that is complementary to a region of a non-coding target nucleic acid sequence of the target gene and optionally comprises a mismatch at the 5' terminal region, and a second ribonucleic acid strand that is complementary to the first strand and optionally comprises a blocking moiety at the 5' terminal region. One aspect the invention provides methods of increasing gene expression by introducing a modified gene-specific saRNA molecule into a cell, wherein the modified saRNA molecule has a first strand that is complementary to a region of a non-coding target nucleic acid sequence of the target gene and optionally comprises a mismatch at the 5' terminal region, and a second ribonucleic acid strand that is complementary to the first strand and optionally comprises a blocking moiety at the 5' terminal region, and wherein the introduction results in an increase in expression of the gene. Increasing gene activity can be useful in the context of a tumor suppressor gene in, for example, inhibition of cellular proliferation, inhibition of cellular transformation and inhibition of cellular migration (e.g., as an anti-cancer agent). In another aspect the invention, compositions, pharmaceutical preparations, and kits comprising at least one modified saRNA molecule are provided.

The invention will now be described in more detail.

Compositions

As noted above the present invention provides modified short activating RNA (saRNA) molecules for use in increasing gene expression in mammalian cells by targeting a region of non-coding nucleic acid sequence of the gene (e.g., a regulatory sequence, an intron, etc.) with an saRNA that has been modified at the 5' terminal region of its antisense strand and/or sense strand.

As used herein the term "saRNA" and the phrase "short activating RNA" refer to a ribonucleic acid molecule capable of promoting gene expression and can be composed of a first ribonucleic acid strand (the "antisense strand") comprising a ribonucleotide sequence complementary to a non-coding nucleic acid sequence of a gene (a "target sequence") and a second ribonucleic acid strand (the "sense strand") comprising a nucleotide sequence complementary to the first strand, wherein the first and second strands form a duplex region. The saRNA can also be composed of as a single strand RNA molecule that forms a duplex, or double-stranded, region, wherein the first region (the "antisense region", or "antisense strand"), comprises a ribonucleotide sequence complementary to a non-coding nucleic acid sequence of the gene, and a second region (the "sense region" or "sense strand"), comprises a ribonucleotide sequence complementary to the first region and forming a duplex region with the first region. A detailed description of saRNAs that may be used as the starting point for modification in the present invention may be found in U.S. Patent Application Publication No. US 2010/0210707, the full disclosure of which is incorporated herein by reference.

The modified saRNA molecules of the present invention include a region of complementarity to a non-coding region of appropriate length to provide for transcriptional activation of an adjacent coding sequence. saRNA molecules also typically include 3' terminal nucleotides which are not complementary to the non-coding sequence. The modified saRNA molecules of the present invention in double-stranded form typically comprises a region of complementarity greater than about 10 base pairs and less than about 50 base pairs in length.

For example, modified saRNA for activation of a human E-cadherin gene, as described in the Examples below, includes a 19 nucleotides region of complementarity to a non-coding region of E-cadherin and two 3' terminal dTs, making the saRNA 21 nucleotides in length overall.

In modified saRNAs of the invention, ribonucleotides of a saRNA molecule, or at least one strand of a duplex saRNA molecule, are modified to improve the ability of the saRNA to promote gene expression from a target sequence. These modifications may include the incorporation of at least one mismatch at the 5' terminal region of the antisense strand, i.e. the ribonucleotide sequence complementary to a target sequence; the conjugation of a blocking moiety at the 5' terminal region of the sense strand, i.e. the ribonucleotide sequence that is complementary to the antisense strand; or both a mismatch at the 5' terminal region of the antisense strand and a blocking moiety at the 5' terminus of the sense strand. saRNA modified in this way increase gene expression more than saRNAs not so modified. In other words, modified saRNA of the present invention exhibit an enhanced efficiency of gene activation. By "enhanced efficiency of gene activation", it is meant that the modified saRNA will demonstrate an enhanced ability to promote/increase gene expression in a cell relative to a control, i.e. the saRNA not so modified. Modified saRNAs of the invention that demonstrate an enhanced efficiency of gene activation have the ability to increase the expression of a target gene that is at least 125% of the ability of a control saRNA, i.e. about 125%, about 150%, about 200%, about 300%, about 400% or more of the ability of a control saRNA. In other words, the modified saRNA enhances or augments the increase in gene expression observed with control saRNA by about 1.25-fold, about 1.5-fold, about 2-fold, about 3-fold, about 4-fold, or more. Often, the methods of the invention provide for an increased efficiency of gene activation that is at least about two-fold or higher than the efficiency of gene activation of the control saRNA.

The nucleotides of the modified saRNA, or at least one strand of a duplex saRNA, may be additionally modified in other ways to provide desired characteristics. For example, the saRNA molecules of the invention can comprise modification of a naturally occurring or non-naturally occurring polynucleotide that provides for enhanced nuclear uptake. An example of a nuclear uptake enhancing modification is a stabilizing modification, such as a modified internucleotide linkage, that confers sufficient stability on a molecule, such as a nucleic acid, to render it sufficiently resistant to degradation (e.g., by nucleases) such that the associated nucleic acid can accumulate in the nucleus of a cell when exogenously introduced into the cell. In this example, entry into the cell's nucleus is facilitated by the ability of the modified nucleic acid to resist nucleases sufficiently well such that an effective concentration of the nucleic acid can be achieved inside the nucleus.

Furthermore, the modified saRNA can be 2'-O-bis(2-hydroxyethoxy) methyl orthoester modified to provide for stability of the ribonucleic acid molecule. Other modification, include, for example a backbone phosphate group modification (e.g., methylphosphonate, phosphorothioate, phosphoroamidate and phosphorodithioate internucleotide linkages), which modifications can, for example, enhance their stability in vivo, making them particularly useful in therapeutic applications. A particularly useful phosphate group modification is the conversion to the phosphorothioate or phosphorodithioate forms of the saRNA. Phosphorothioates and phosphorodithioates are more resistant to degradation in vivo than their unmodified oligonucleotide counterparts, increasing the half-lives of the saRNA making them more available to the subject being treated. A saRNA may also be modified to comprise N3'-P5' (NP) phosphoramidate, morpholino phosphorociamidate (MF), locked nucleic acid (LNA), 2'-O-methoxyethyl (MOE), or 2'-fluoro, arabino-nucleic acid (FANA), which can enhance the resistance of the polynucleotide to nuclease degradation (see, e.g., Faria et al. (2001) *Nature Biotechnol.* 19:40-44; Toulme (2001) *Nature Biotechnol.* 19:17-18).

The modified saRNA may be synthesized by any method that is now known or that comes to be known for synthesizing saRNA molecules and that from reading this disclosure, one skilled in the art would conclude would be useful in connection with the present invention. For example, one may use methods of chemical synthesis such as methods that employ Dharmacon, Inc.'s proprietary ACE® technology. Alternatively, one could also use template dependant synthesis methods. Synthesis may be carried out using modified or non-modified, natural or non-natural bases as disclosed herein. Moreover, synthesis may be carried out with or without modified or non-modified nucleic acid backbone as disclosed herein. When synthesized outside of a host cell, e.g. chemically synthesized, or transcribed in vitro, the saRNA is introduced directly to the cell as an RNA molecule, i.e. it is transfected directly into the cell.

Alternatively, the modified saRNA molecules may be synthesized in a host cell by any method that is now known or that comes to be known for synthesizing saRNA molecules in a host cell. For example, saRNA molecules can be expressed from recombinant circular or linear DNA vector using any suitable promoter. Suitable promoters for expressing saRNA molecules of the invention from a vector include, for example, the U6 or H1 RNA pol III promoter sequences and the cytomegalovirus promoter. Selection of other suitable promoters is within the skill in the art. Suitable vectors for use with the subject invention include those described in U.S. Pat. No. 5,624,803, the disclosure of which is incorporated herein in its entirely. The recombinant plasmids of the invention can also comprise inducible or regulatable promoters for expression of the saRNA molecule in a particular tissue or in a particular intracellular environment.

The modified saRNA molecules of the invention can be expressed from one or more recombinant nucleic acid vectors either as two separate, complementary RNA molecules, or as a single RNA molecule with two complementary regions. The nucleic acid vectors may be plasmids, minicircle DNAs, virus-delivered vectors such as cytomegalovirus, adenovirus, etc, or they may be integrated in to the target cell genome through homologous recombination or random integration, e.g. retrovirus derived vectors such as MMLV, HIV-1, ALV, etc. Methods for contacting cells with nucleic acid vectors, such as electroporation, calcium chloride transfection, and lipofection, are well known in the art, as are methods for infecting cells with viruses comprising viral particles carrying saRNA-encoding sequence. Selection of vectors suitable for expressing saRNA of the invention, methods for inserting nucleic acid sequences for expressing the saRNA into the vector, and methods of delivering the recombinant vector to the cells of interest are within the skill in the art. See, for example Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat. Biotechnol. 20: 505-508, the entire disclosures of which are herein incorporated by reference. Other methods for delivery and intracellular expression suitable for use in the invention are described in, for example, U.S. Patent Application Publication Nos. 20040005593, 20050048647, 20050060771, the entire disclosures of which are herein incorporated by reference.

Once synthesized, the modified saRNA of the present invention may immediately be used or be stored for future use. In some embodiments, the modified saRNA of the invention are stored as duplexes in a suitable buffer. Many buffers are known in the art suitable for storing saRNAs. For example, the buffer may be comprised of 100 mM KCl, 30 mM HEPES-pH 7.5, and 1 mM $MgCl_2$. In representative embodiments, the double stranded polynucleotides of the present invention retain 30% to 100% of their activity when stored in such a buffer at 4° C. for one year. More preferably, they retain 80% to 100% of their biological activity when stored in such a buffer at 4° C. for one year. Alternatively, the compositions can be stored at −20° C. in such a buffer for at least a year or more. Usually, storage for a year or more at −20° C. results in less than a 50% decrease in biological activity. More usually, storage for a year or more at −20° C. results in less than a 20% decrease in biological activity after a year or more. Furthermore, storage for a year or more at −20° C. results in less than a 10% decrease in biological activity.

In order to ensure stability of the modified saRNA prior to usage, they may be retained in dry form (e.g., lyophilized form) at −20° C. until they are ready for use. Prior to usage, they should be resuspended; however, even once resuspended, for example, in the aforementioned buffer, they should be kept at −20° C. until used. The aforementioned buffer, prior to use, may be stored at approximately 4° C. or room temperature. Effective temperatures at which to conduct transfection are well known to persons skilled in the art, but include for example, room temperature.

Methods

The present invention provides methods of increasing gene expression comprising introducing a modified saRNA molecule into a cell's nucleus, wherein the modified saRNA molecule comprises a mismatch at the 5' terminal region of the antisense strand and/or a blocking moiety at the 5' terminal region of the sense strand of the saRNA. In general, "increasing gene expression" refers to an increase in the gene's ability to be transcribed, its ability to be translated and result in expression of a protein, regardless of the mechanism whereby such activation occurs. Modified saRNAs of the present invention have an enhanced efficiency for increasing gene expression relative to saRNAs not so modified.

In general, the methods of the present invention are carried out by contacting a cell with a modified saRNA molecule, wherein the modified saRNA molecule comprises a first ribonucleic acid strand comprising a ribonucleotide sequence complementary to a non-coding nucleic acid sequence of a gene and optionally comprising a mismatch at the 5' terminal region, a second ribonucleic acid strand comprising a nucleotide sequence complementary to the first strand and optionally comprising a blocking moiety at the 5' terminal region, wherein the first and second strands form a duplex region of between about 15 to about 30 base pairs in the modified saRNA molecule, wherein the introduction results in an increase in expression of the gene.

In representative embodiments, an increase in gene expression results in at least about a 2-fold increase or more in transcription associated with a nucleic acid sequence, as compared to a control, e.g., in the absence of any saRNA molecule. In some embodiments, the increase in gene expression results in at least about a 2.5-fold increase or more, at least about a 3-fold increase or more, at least about a 3.5-fold increase or more, at least about a 4-fold increase or more, at least about a 4.5-fold increase or more, at least about a 5-fold increase or more, at least about a 5.5-fold increase or more, at least about a 6-fold increase or more, at least about a 6.5-fold increase or more, at least about a 7-fold increase or more, at least about a 7.5-fold increase or more at least about a 8-fold increase or more, and up to about 10-fold increase or more, including about 15-fold increase or more, about 20-fold increase or more, such as 25-fold increase or more. The increase in expression is usually observed about 48 hours or more after contacting the cells with the modified saRNA molecule, i.e. 24, 30, or 36 hours following contact, more usually 42, 48, 54, 60 or 72 hours after contact. The increase in expression is usually maintained for at least 12 days after contact, i.e. at least 11, 12, 13, or 14 days, sometimes as much as 15, 16, 17, 18 days or more. In other words, increased expression is usually maintained for at least about 8 or 9 days, more usually 10 days, sometimes as much as 11, 12, 13, or 14 days or more.

Additionally, modified saRNA of the present invention increase gene expression to a greater extent than saRNA that does not comprise mismatch modification at the 5' terminal region of the antisense strand or a blocking moiety at the 5' terminal region of the sense strand. In other words, modified saRNA of the present invention exhibit an enhanced efficiency of gene activation. By "enhanced efficiency of gene activation", it is meant that the modified saRNA will demonstrate an enhanced ability to promote/increase gene expression in a cell relative to a control, i.e. the saRNA not so modified. Modified saRNAs of the invention that demonstrate an enhanced efficiency of gene activation have the ability to increase the expression of a target gene that is at least 125% of the ability of a control saRNA, i.e. about 125%, about 150%, about 200%, about 300%, about 400% or more of the ability of a control saRNA. In other words, the modified saRNA enhances/augments the increase in gene expression observed with control saRNA by about 1.25-fold, about 1.5-fold, about 2-fold, about 3-fold, about 4-fold, or more. Usually, the methods of the invention provide for an increased efficiency of gene activation that is at least about two-fold or higher than the efficiency of gene activation of the saRNA.

An increase in gene expression or activity can be measured by any of a variety of methods well known in the art. Suitable methods of examining gene expression or activity include measuring nucleic acid transcription level, mRNA level, enzymatic activity, methylation state, chromatin state or configuration, or other measure of nucleic acid activity or state in a cell or biological system.

After introduction of a modified saRNA molecule into a cell, the introduction results in a decrease in histone methylation (e.g., at a lysine). Accordingly, introduction of the modified saRNA molecule in the cell results in demethylation of a histone molecule, such as histone 3, usually at the lysine residue, e.g., a lysine 9 residue.

Because the ability of the modified saRNAs of the present invention to retain functionality and resist degradation of the compound is not dependent on the sequence of the bases, the cell type, or the species into which it is introduced, the present invention is applicable across a broad range of mammals, including but not limited to humans. The present invention is particularly advantageous for use in mammals such as cattle, horse, goats, pigs, sheep, canines, rodents such as hamsters, mice, and rats, and primates such as, for example, gorillas, chimpanzees, and humans. Transgenic mammals may also be used, e.g. mammals that have a chimeric gene sequence. Methods of making transgenic animals are well known in the art, see, for example, U.S. Pat. No. 5,614,396.

The present invention may be used advantageously with diverse cell types from any of the the aforementioned species including those of the germ cell line, as well as somatic cells. The cells may be stem cells or differentiated cells. For example, the cell types may be embryonic cells, oocytes sperm cells, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes and cells of the endocrine or exocrine glands.

The present invention is applicable for use for activation (e.g., increasing expression) of a broad range of genes, including but not limited to the genes of a human genome, such as those implicated in diseases such as diabetes, Alzheimer's and cancer, as well as all genes in the genomes of the aforementioned organisms. Furthermore, the compositions and methods of the present invention may also be used to target a recombinant gene, such as a gene introduced on a nucleic acid vector.

The compositions and methods of the present invention may be administered to a cell or applied by any method that is now known or that comes to be known and that from reading this disclosure, one skilled in the art would conclude would be useful with the present invention. For example, the polynucleotides may be passively delivered to cells.

Passive uptake of modified polynucleotides can be modulated, for example, by the presence of a conjugate such as a polyethylene glycol moiety or a cholesterol moiety at the 5' terminal of the sense strand and/or, in appropriate circumstances, a pharmaceutically acceptable carrier.

The modified saRNA may be delivered to a cell by any method that is now known or that comes to be known and that from reading this disclosure, persons skilled in the art would determine would be useful in connection with the present invention in enabling modified saRNA to cross the cellular membrane and/or the nuclear membrane. These methods include, but are not limited to, any manner of transfection, such as for example transfection employing DEAE-Dextran, calcium phosphate, cationic lipids/liposomes, micelles, manipulation of pressure, microinjection, electroporation, immunoporation, use of vectors such as viruses (e.g., RNA virus), plasmids, cell fusions, and coupling of the polynucleotides to specific conjugates or ligands such as antibodies, antigens, or receptors, passive introduction, adding moieties to the modified saRNA that facilitate its uptake, and the like.

The stabilized modified saRNAs of the present invention may be used in a diverse set of applications, including but not limited to basic research, drug discovery and development, diagnostics and therapeutics. For example, the present invention may be used to validate whether a gene product is a target for drug discovery or development. In this application, a target nucleic acid sequence of interest is identified for activation (e.g., increasing expression). For example, a cell is contacted with a modified saRNA specific for targeting the regulatory sequence of the particular target sequence of interest. The cell is maintained under conditions allowing for the methylation of the targeted DNA and/or methylation of nuclear proteins such as, for example, one or more histones, resulting in decreased activity or transcription of a gene. The extent of any increased activity, such as, for example, transcription or translation, of the gene is then assessed, along with the effect of such increased activity, and a determination is made that if activity is increased, then the nucleic acid sequence of interest is a target for drug discovery or development. In this manner, phenotypically desirable effects can be associated with modified saRNA activation of particular target nucleic acids of interest, and in appropriate cases toxicity and pharmacokinetic studies can be undertaken and therapeutic preparations developed.

The present invention may also be used in applications that induce transient or permanent states of disease or disorder in an organism by, for example, increasing the activity (e.g., by increasing transcription or translation) of a target nucleic acid of interest believed to be a cause or factor in the disease or disorder of interest in order to provide an animal model of a disease or disorder. Increased activity of the target nucleic acid of interest may render the disease or disorder worse, or tend to ameliorate or to cure the disease or disorder of interest, as the case may be. Likewise, increased activity of the target nucleic acid of interest may cause the disease or disorder, render it worse, or tend to ameliorate or cure it, as the case may be. Target nucleic acids of interest can comprise genomic or chromosomal nucleic acids or extrachromosomal nucleic acids, such as viral nucleic acids. Target nucleic acids of interest can include all manner of nucleic acids, such as, for example, non-coding DNA, regulatory DNA, repetitive DNA, reverse repeats, centromeric DNA, DNA in euchromatin regions, DNA in heterochromatin regions, promoter sequences, enhancer sequences, introns sequences, exon sequences, and the like.

Still further, the present invention may be used in applications, such as diagnostics, prophylactics, and therapeutics. For these applications, an organism suspected of having a disease or disorder that is amenable to modulation by manipulation of a particular target nucleic acid of interest is treated by administering modified saRNA. Results of the modified saRNA treatment may be ameliorative, palliative, prophylactic, and/or diagnostic of a particular disease or disorder. In representative embodiments, the modified saRNA is administered in a pharmaceutically acceptable manner with a pharmaceutically acceptable carrier with or without a diluent.

In some embodiments increasing expression of tumor suppressor genes is desirable. As such, agents that act to increase gene activity in such genes are useful in the treatment of a cellular proliferative disease, e.g., any condition, disorder or disease, or symptom of such condition, disorder, or disease that results from the uncontrolled proliferation of cells, e.g., cancer. Cancer is an example of a condition that is treatable using the compounds of the invention. Use of the modified saRNAs of the invention in combination with a second compound for use in treatment of a cellular proliferative disease is of particular interest. Exemplary cancers suitable for treatment with the subject methods include colorectal cancer, non-small cell lung cancer, small cell lung cancer, ovarian cancer, breast cancer, head and neck cancer, renal cell carcinoma, and the like.

Exemplary tumor suppressor genes include, but are not limited to, p53, p21, BRCA1, BRCA2, APC, RB1, CDKN2A, DCC, DPC4 (SMAD4), MADR2/JV18 (SMAD2), MEN1, MTS1, NF1, NF2, PTEN, VHL, WRN, and WT1. Other genes of interest include, but are not limited to, the nitric oxide synthase (NOS) genes, including NOS1 (nNOS) and NOS3 (eNOS), e-cadherin, growth factors, such as vascular endothelial growth factor (VEGF), neuronal growth factor (NGF), and the like.

Subjects suitable for treatment with a method of the present invention involving modified saRNAs include individuals having a cellular proliferative disease, such as a neoplastic disease (e.g., cancer). Cellular proliferative disease is characterized by the undesired propagation of cells, including, but not limited to, neoplastic disease conditions, e.g., cancer. Examples of cellular proliferative disease include, but are not limited to, abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying, for example, rheumatoid arthritis, psoriasis, diabetic retinopathy, other ocular angiogenic diseases such as retinopathy of prematurity (retrolental fibroplastic), macular degeneration, corneal graft rejection, neuroscular glaucoma and Oster Webber syndrome, psoriasis, restinosis, fungal, parasitic and viral infections such as cytomegaloviral infections. Subjects to be treated according to the methods of the invention include any individual having any of the above-mentioned disorders.

The invention should not be construed to be limited solely to the treatment of patients having a cellular proliferative disease. Rather, the invention should be construed to include the treatment of patients having conditions or disease associated with decreased expression of particular genes that would benefit from the methods of the subject invention.

Such subjects may be tested in order to assay the activity and efficacy of the subject modified saRNAs. Significant improvements in one or more of parameters is indicative of efficacy. It is well within the skill of the ordinary healthcare worker (e.g., clinician) to adjust dosage regimen and dose amounts to provide for optimal benefit to the patient according to a variety of factors (e.g., patient-dependent factors such as the severity of the disease and the like, the compound administered, and the like).

Pharmaceutical Preparations Containing Compounds of the Invention

Also provided by the invention are pharmaceutical preparations of the subject modified saRNA compounds described above. The subject modified saRNA compounds can be incorporated into a variety of formulations for therapeutic administration by a variety of routes. More particularly, the compounds of the present invention can be formulated into pharmaceutical compositions by combination with appropriate, pharmaceutically acceptable carriers, diluents, excipients and/or adjuvants, and may be formulated into preparations in solid, semi-solid, liquid or gaseous forms, such as tablets, capsules, powders, granules, ointments, solutions, suppositories, injections, inhalants and aerosols, in a sterile vial or in a syringe. Where the formulation is for transdermal administration, the compounds are preferably formulated either without detectable DMSO or with a carrier in addition to DMSO. The formulations may be designed for administration to subjects or patients in need thereof via a number of different routes, including oral, buccal, rectal, parenteral, intraperitoneal, intradermal, intratracheal, etc. The administration can be systemic or localized delivery of the formulation to a site in need of treatment, e.g., localized delivery to a tumor.

Pharmaceutically acceptable excipients usable with the invention, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

Dosage Forms of Compounds of the Invention

In pharmaceutical dosage forms, the subject modified saRNA compounds of the invention may be administered in the form of their pharmaceutically acceptable salts, or they may also be used alone or in appropriate association, as well as in combination, with other pharmaceutically active compounds. The following methods and excipients are merely exemplary and are in no way limiting.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes, such as intrapulmonary or intranasal delivery.

Conventional and pharmaceutically acceptable routes of administration include intranasal, intrapulmonary, intramuscular, intratracheal, intratumoral, intraventricular, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

For oral preparations, the subject modified saRNA compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Parenteral routes of administration other than inhalation administration include, but are not necessarily limited to, topical, transdermal, subcutaneous, intramuscular, intraorbital, intraventricular, intracapsular, intraspinal, intrasternal, intravenous routes, i.e., any route of administration other than through the alimentary canal, and local injection, with intra or peritumoral injection being of interest, especially where a tumor is a solid or semi-solid tumor (e.g., Hodgkins lymphoma, non-Hodgkins lymphoma, and the like). Local injection into a tissue defining a biological compartment (e.g., prostate, ovary, regions of the heart (e.g., pericardial space defined by the pericardial sac), intrathecal space, synovial space, and the like) is also of interest. Parenteral administration can be carried to effect systemic or local delivery of the agent. Where systemic delivery is desired, administration typically involves invasive or systemically absorbed topical or mucosal administration of pharmaceutical preparations.

For some conditions, particularly central nervous system conditions, it may be necessary to formulate the modified saRNA to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of modified saRNA behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the saRNA has been reversably affixed (see e.g. US Application Nos. 20080081064 and 20090196903, incorporated herein by reference).

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

The subject modified saRNA compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol, collagen, cholesterol; and if desired, with conventional additives such as solubilizers, isotonic agents, suspending agents, emulsifying agents, stabilizers and preservatives.

The modified saRNA compounds can also be delivered to the subject by enteral administration. Enteral routes of administration include, but are not necessarily limited to, oral and rectal (e.g., using a suppository) delivery.

Furthermore, the subject modified saRNA compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Dosages of the Compounds of the Invention

Depending on the subject and condition being treated and on the administration route, the subject modified saRNA compounds may be administered in dosages of, for example, 0.1 µg to 100 mg/kg body weight per day. In certain embodiments, the therapeutic administration is repeated until a desired effect is achieved. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Dosages for a given compound are readily determinable by those of skill in the art by a variety of means.

Although the dosage used will vary depending on the clinical goals to be achieved, a suitable dosage range is one which provides up to about 1 µg to about 1,000 µg or about 10,000 µg of subject composition to reduce a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

Combination Therapy Using the Compounds of the Invention

For use in the subject methods, the subject compounds may be formulated with or otherwise administered in combination with other pharmaceutically active agents, including other agents that activate or suppress a biochemical activity, such as a chemotherapeutic agent. The subject compounds may be used to provide an increase in the effectiveness of another chemical, such as a pharmaceutical, or a decrease in the amount of another chemical, such as a pharmaceutical that is necessary to produce the desired biological effect.

Examples of chemotherapeutic agents for use in combination therapy include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES).

Furthermore the modified saRNA compounds of the present invention may also be used in combination therapy with saRNA molecules not so modified. In such embodiments, the modified saRNA molecules may be administered to increase expression of a first gene and the saRNA molecule may be administered to increase expression of a second gene.

Furthermore, the modified saRNA compounds of the present invention may also be used in combination therapy with siRNA molecules. In such embodiments, the modified saRNA molecules may be administered to increase activation of a first gene and the siRNA molecule may be administered to silence expression of a second gene. For example, the modified saRNA molecules may be administered to increase activation of a tumor suppressor gene and the siRNA molecule may be administered to silence expression of an oncogene.

The compounds described herein for use in combination therapy with the compounds of the present invention may be administered by the same route of administration (e.g. intrapulmonary, oral, enteral, etc.) that the compounds are administered. In the alternative, the compounds for use in combination therapy with the compounds of the present invention may be administered by a different route of administration that the compounds are administered.

Kits

Kits with unit doses of the subject compounds, usually in oral or injectable doses, are provided. In such kits, in addition to the containers containing the unit doses will be an informational package insert describing the use and attendant benefits of the drugs in treating pathological condition of interest. Representative compounds and unit doses are those described herein above.

In one embodiment, the kit comprises a modified saRNA formulation in a sterile vial or in a syringe, which formulation can be suitable for injection in a mammal, particularly a human. Examples of modified saRNAs that may be provided in such kits include modified saRNA that is specific for the E-cadherin gene and modified saRNA that is specific for the p21gene, as described in greater detail in the examples section below.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following methods and materials were used in the examples.

Cell Culture and dsRNA Transfection.

PC-3, HeLa, and A498 cells were maintained in RPMI 1640 medium supplemented with 10% FBS, L-glutamine (2 mM), penicillin (100 U/ml) and streptomycin (100 µg/ml) in a humidified atmosphere of 5% CO2 at 37° C. The day before transfection, cells were plated in growth medium without antibiotics at a density of ~50-60%. Transfection of saRNA and/or siRNA was carried out using Lipofectamine RNAiMax (Invitrogen, Carlsbad, Calif.) according to the manufacturer's instructions. All siRNAs, unmodified saRNAs, biotin-linked duplexes, and mismatched derivates were synthesized by Invitrogen. The 2'-OMe-modified saRNA molecules were synthesized by Dharmacon (Lafayette, Colo.). Sequences are described in Table 1 below.

TABLE 1

Duplex RNAs and oligonucleotide sequences.

| saRNA/siRNA | Sequence (5'-3')* | SEQ ID NO: |
|---|---|---|
| siMOF S | GUGAUCCAGUCUCGAGUGAUU | 1 |
| siMOF AS | UCACUCGAGACUGGAUCACUU | 2 |
| siE2F1 S | UGGACUCUUCGGAGAACUU[dT][dT] | 3 |
| siE2F1 AS | AAGUUCUCCGAAGAGUCCA[dT][dT] | 4 |
| siAgo1 S | GAGAAGAGGUGCUCAAGAA[dT][dT] | 5 |
| siAgo1 AS | UUCUUGAGCACCUCUUCUC[dT][dT] | 6 |
| siAgo2 S | GCACGGAAGUCCAUCUGAA[dT][dT] | 7 |
| siAgo2 AS | UUCAGAUGGACUUCCGUGC[dT][dT] | 8 |
| siAgo3 S | GAAAUUAGCAGAUUGGUAA[dT][dT] | 9 |
| siAgo3 AS | UUACCAAUCUGCUAAUUUC[dT][dT] | 10 |
| siAgo4 S | GGCCAGAACUAAUAGCAAU[dT][dT] | 11 |
| siAgo4 AS | AUUGCUAUUAGUUCUGGCC[dT][dT] | 12 |

TABLE 1-continued

Duplex RNAs and oligonucleotide sequences.

| | | |
|---|---|---|
| siCon S | UUCUCCGAACGUGUCACGU[dT][dT] | 13 |
| siCon AS | ACGUGACACGUUCGGAGAA[dT][dT] | 14 |
| dsEcad-215 S | AACCGUGCAGGUCCCAUAA[dT][dT] | 15 |
| dsEcad-215 AS | UUAUGGGACCUGCACGGUU[dT][dT] | 16 |
| dsP21-322 S | CCAACUCAUUCUCCAAGUA[dT][dT] | 17 |
| dsP21-322 AS | UACUUGGAGAAUGAGUUGG[dT][dT] | 18 |
| dsControl S | ACUACUGAGUGACAGUAGA[dT][dT] | 19 |
| dsControl AS | UCUACUGUCACUCAGUAGU[dT][dT] | 20 |
| dsEcad-215-S-5'Bio S | Bio-AACCGUGCAGGUCCCAUAA[dT][dT] | 21 |
| dsEcad-215-S-5'Bio AS | UUAUGGGACCUGCACGGUU[dT][dT] | 16 |
| dsEcad-215-AS-5'Bio S | AACCGUGCAGGUCCCAUAA[dT][dT] | 15 |
| dsEcad-215-AS-5'Bio AS | Bio-UUAUGGGACCUGCACGGUU[dT][dT] | 22 |
| dsP21-322-S-5'Bio S | Bio-CCAACUCAUUCUCCAAGUA[dT][dT] | 23 |
| dsP21-322-S-5'Bio AS | UACUUGGAGAAUGAGUUGG[dT][dT] | 18 |
| dsP21-322-AS-5'Bio S | CCAACUCAUUCUCCAAGUA[dT][dT] | 17 |
| dsP21-322-AS-5'Bio AS | Bio-UACUUGGAGAAUGAGUUGG[dT][dT] | 24 |
| dsEcad-215-S-MM S | AACCGUGCAGGUCCCAUAA[dT][dT] | 15 |
| dsEcad-215-S-MM AS | UUAUGGGACCUGCACGGUA[dT][dT] | 24 |
| dsEcad-215-AS-MM S | AACCGUGCAGGUCCCAUAU[dT][dT] | 25 |
| dsEcad-215-AS-MM AS | UUAUGGGACCUGCACGGUU[dT][dT] | 16 |
| dsP21-322-S-MM S | CCAACUCAUUCUCCAAGUA[dT][dT] | 17 |
| dsP21-322-S-MM AS | UACUUGGAGAAUGAGUUGC[dT][dT] | 26 |
| dsP21-322-AS-MM S | CCAACUCAUUCUCCAAGUU[dT][dT] | 27 |
| dsP21-322-AS-MM AS | UACUUGGAGAAUGAGUUGG[dT][dT] | 18 |
| dsP21-322-AS-5'Bio-S-MM S | CCAACUCAUUCUCCAAGUU[dT][dT] | 27 |
| dsP21-322-AS-5'Bio-S-MM AS | Bio-UACUUGGAGAAUGAGUUGG[dT][dT] | 24 |
| dsP21-322-S-2'OMe S | CCAACUCAmUmUCUCCAAGUA[dT][dT] | 28 |
| dsP21-322-S-2'OMe AS | UACUUGGAGAAUGAGUUGG[dT][dT] | 18 |
| dsP21-322-AS-2'OMe S | CCAACUCAUUCUCCAAGUA[dT][dT] | 17 |
| dsP21-322-AS-2'OMe AS | UACUUGGAmGmAAUGAGUUGG[dT][dT] | 29 |
| dsEcad-215-3'Bio S | AACCGUGCAGGUCCCAUAA[dT][dT]-Bio | 30 |
| dsEcad-215-3'Bio AS | UUAUGGGACCUGCACGGUU[dT][dT]-Bio | 31 |
| dsEcad-215-S-5'Bio-AS-MM S | Bio-AACCGUGCAGGUCCCAUAU[dT][dT] | 32 |
| dsEcad-215-S-5'Bio-AS-MM AS | UUAUGGGACCUGCACGGUU[dT][dT] | 16 |
| dsP21-322- S-5'Bio-AS-MM S | Bio-CCAACUCAUUCUCCAAGUU[dT][dT] | 33 |
| dsP21-322- S-5'Bio-AS-MM AS | UACUUGGAGAAUGAGUUGG[dT][dT] | 18 |
| RT-PCR Primers | Sequence (5'-3') | |
| E-cadherin S | CCTGGGACTCCACCTACAGA | 34 |
| E-cadherin AS | GGATGACACAGCGTGAGAGA | 35 |

TABLE 1-continued

Duplex RNAs and oligonucleotide sequences.

| | | |
|---|---|---|
| p21 S | GCCCAGTGGACAGCGAGCAG | 36 |
| p21 AS | GCCGGCGTTTGGAGTGGTAGA | 37 |
| MOF S | ATCCACATCGGGAACTACGA | 38 |
| MOF AS | TCTTTGCCATCAACTTCGTG | 39 |
| E2F1 S | CATCTATGACATCACCAACGTC | 40 |
| E2F1 AS | GCTTTGATCACCATAACCATCT | 41 |
| Ago1 S | GCGAATTGGGAAGAGTGGTA | 42 |
| Ago1 AS | GCAGGTGCTGGGATAGAGAC | 43 |
| Ago2 S | CGCGTCCGAAGGCTGCTCTA | 44 |
| Ago2 AS | TGGCTGTGCCTTGTAAAACGCT | 45 |
| Ago3 S | ATCCCAGCTGGAACAACAGT | 46 |
| Ago3 AS | GCGTACGTAAGTGTGGCAGA | 47 |
| Ago4 S | GGGTAGGGAAAAGTGGCAAT | 48 |
| Ago4 AS | GAGCGAGTGCACCTCACATA | 49 |
| GAPDH S | TCCCATCACCATCTTCCA | 50 |
| GAPDH AS | CATCACGCCACAGTTTCC | 51 |
| pMIR Insert Sequences | Sequence (5'-3') | |
| pOffTar S | CTAGTAGATCTTGTGTGTGTGTTATGGGACCTGCACGGTTGAACATACACA | 52 |
| pOffTar AS | AGCTTGTGTATGTTCAACCGTGCAGGTCCCATAACACACACAAGATCTA | 53 |
| pNonSpec S | CTAGTAGATCTTGTGTGTGTGGGTAGGCGTCAAGTAGATAGCGAACATACACA | 54 |
| pNonSpec AS | AGCTTGTGTATGTTCGCTATCTACTTGACGCCTACCCACACACAAGATCTA | 55 |

*Bio: biotin, m: 2'-O-Methyl

Analysis and quantification of mRNA expression.

Total RNA was extracted using the RNeasy RNA isolation kit (Qiagen, Velencia, CA) according to the manufacturer's protocol. One microgram of total RNA was reverse transcribed using the Reverse Transcription System (Promega, Madison, Wis.) with oligo(dT) primers. The resulting cDNA samples were amplified by PCR using primers specific for E-cadherin, p21, MOF, E2F1, Ago1-4, or GAPDH (Table 1) and visualized on an agarose gel. Optical densitometry was utilized to quantify relative abundance of each gene transcript in order to evaluate RNAa or RNAi kinetics. GAPDH served as an endogenous control used to normalize data. RNAa activity of the E-cadherin saRNA molecules and efficiency of the MOF and E2F1 siRNAs was quantified by real-time PCR. Gene-specific TaqManÒ assay kits (Applied Biosystems, Foster City, Calif.) for E-cadherin, MOF, E2F1, and GAPDH were used in conjunction with the 7300 Real-Time System (Applied Biosystems) to measure relative transcript levels. Each sample was analyzed in quadruplicate and GAPDH levels were utilized to normalize data. Relative expression and standard error were calculated by the supplied 7300 Real-Time System software.

Immunoblotting.

Cultured cells were washed with cold phosphate buffered saline (PBS) buffer and lysed with M-PER protein extraction buffer (Pierce, Rockford, Ill.) containing protease inhibitors. Cell lysates were centrifuged and supernatants were collected. Equal quantities of protein were resolved by electrophoresis on sodium dodecyl sulfate (SDS) polyacrylamide gels and transferred to 0.45 mm nitrocellulose membranes by voltage gradient. The resulting blots were blocked with 5% non-fat dry milk and probed with primary antibodies specific to E-cadherin (Zymed, South San Francisco, Calif.) or GAPDH (Chemicon, Temecula, Calif.) Immunodetection occurred by incubating blots with appropriate secondary HRP-linked antibodies and utilizing chemiluminescence to visualize the antigen-antibody complexes. GAPDH served as an internal control.

Analysis of Off-Target Activity.

A target site complementary to the sense strand of dsEcad-215 (pOffTar) was cloned into the 3'UTR of the pMIR-Report luciferase reporter vector (Ambion, Foster City, Calif.) in order quantify the off-target activity of dsEcad-215 and its modified variants (e.g. dsEcad-215-S-5'Bio-AS-MM, etc.). A non-specific site (pNonSpec) was also cloned to serve as a control for specificity. All oligonucleotide sequences used to create the 3'UTR constructs are listed in Table 1. PC-3 cells were transfected with 0.6 μg pOffTar or pNonSpec, 0.4 μg pMIR-Report Beta-gal, and 30 nM dsRNA for 24 hours. The pMIR-Report Beta-gal vector served as a control to monitor transfection efficiency. The Dual-Light System® chemiluminescent reporter gene assay (Applied Biosystems) was used to quantify luciferase and β-galactosidase activity. Off-target activity was confirmed by a reduction in luciferase activity.

Results

Figure 1:
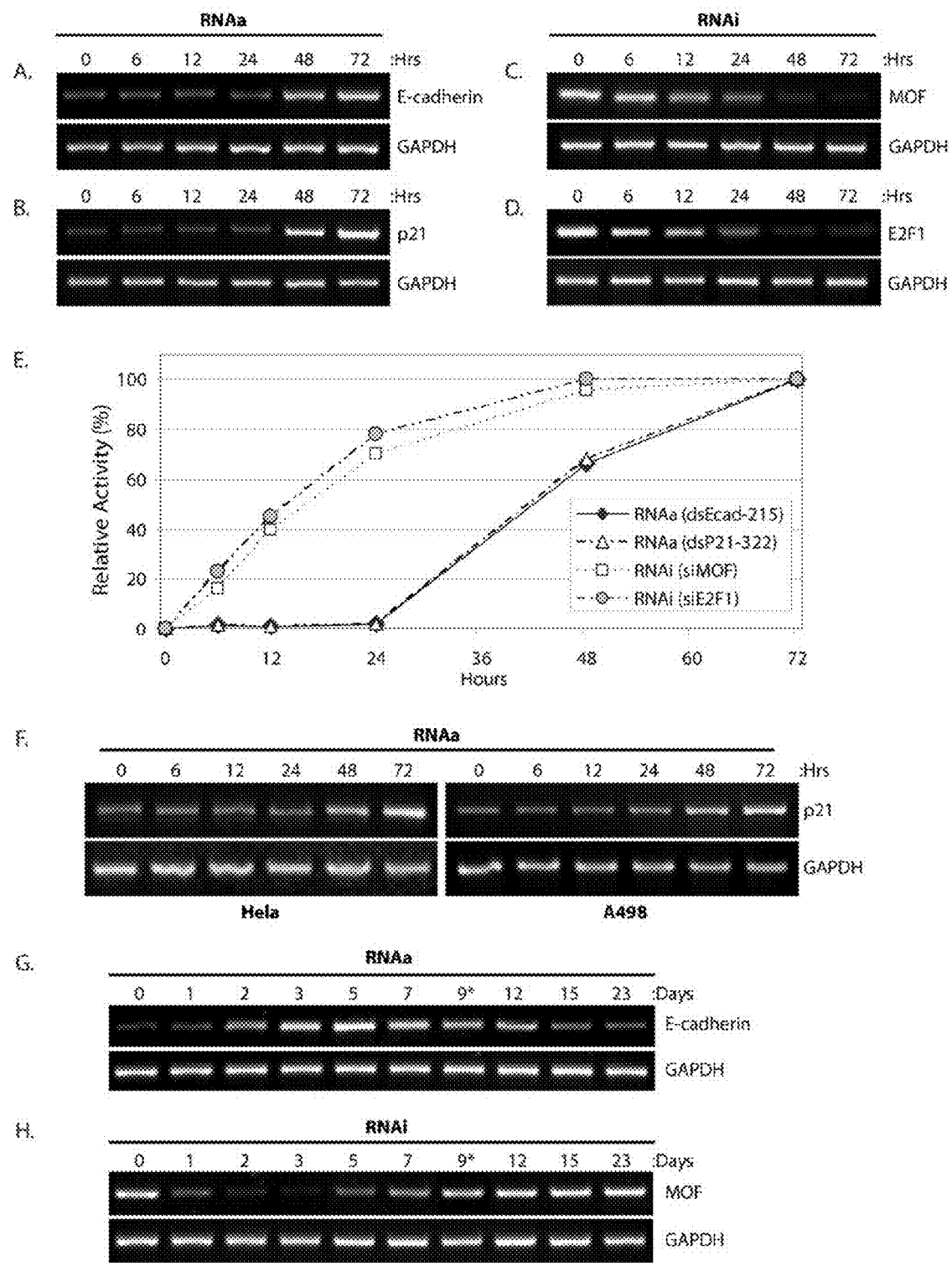
FIG. 1 demonstrates the kinetics of RNAa and RNAi activity as assessed by RT-PCR.

The kinetics of gene induction by RNAa. It has been shown that E-cadherin and p21 are susceptible to RNAa in a variety of cells lines including PC-3 (prostate adenocarcinoma) cells (Li, L. C., et al. (2006) Proc Natl Acad Sci USA 103, 17337-42; Chen, Z., et al. (2008) Mol Cancer Ther 7, 698-703). In order to evaluate the rate of gene induction, PC-3 cells were transfected with saRNAs targeting a sequence within the promoter of the E-cadherin gene at position-215 relative to the transcriptional start site of E-cadherin ("dsEcad-215") or a sequence within the promoter of the p21Waf1/Cip1/Sdi1 (p21) gene at position-322 relative to the transcriptional start site of p21(dsP21-322) and gene induction was monitored throughout a 72-hour time course. As shown in FIG. 1A-B, induction of E-cadherin and p21 expression began to emerge following 48 hours of saRNA transfection with levels continuing to increase by 72 hours. To compare the kinetics of RNAa to RNAi, PC-3 cells were transfected with siRNA targeting the MOF (siMOF) or E2F1 (siE2F1) gene transcripts and the rate of mRNA knockdown observed. Unlike RNAa, knockdown by RNAi was observed as early as 6 hours with levels almost maximally subsiding by ~24 hours following siRNA transfection (FIG. 1C-D). MOF and E2F1 were selected as suitable targets to monitor RNAi activity based on specific and efficient knockdown by their corresponding siRNAs; MOF and E2F1 were downregulated >80% following 72 hours of siRNA transfection (FIG. 6).

The expression levels of each transcript following saRNA or siRNA transfection was quantified and used to calculate the relative activity of RNAa and RNAi, respectively, at each individual time point to allow for the direct comparison of RNAa and RNAi kinetics in PC-3 cells. As shown in FIG. 1E, the rate at which RNAa activity emerges is delayed by ~24-48 hours in comparison to RNAi.

In addition, HeLa (cervix adenocarcinoma) and A498 (kidney carcinoma) cell lines were transfected with dsP21-322 and p21 induction monitored. In both cell lines, induction of p21 was detectable by ~48 hours (FIG. 1F). These results indicate that the delayed response in RNAa activity in comparison to RNAi is a general feature of RNAa and not specific to any particular cell line. Taken together, these results indicate that the emergence of RNAa activity occurs at a different rate than RNAi, emerging ~48 hours after initial treatments.

To compare the duration of RNAa and RNAi activity, PC-3 cells were transfected with dsEcad-215 or siMOF for up to 23 days and E-cadherin and MOF transcript levels monitored, respectively. As shown in FIG. 1G, induction of E-cadherin was observed at days ~2-12 with optimal levels of induction between days 3-7. Remarkably, E-cadherin induction was detectable through cell passage, which occurred prior to day 9 (see asterisk). Knockdown of MOF was observed at days ~1-7 with optimal activity between days 1-3 (FIG. 1H). MOF levels quickly rebounded following passage of cells at day 9. This data indicates that the optimal window for RNAa activity is between days ~3-7 and generally lasted longer (~10 days) than RNAi activity (~7 days) in PC-3 cells.

Ago2 is required for RNAa activity. The Argonaute (Ago) family of proteins are key regulators of RNAi that function, in part, by recruiting small dsRNAs (Meister, G., et al. (2004) Mol Cell 15, 185-97; Diederichs, S. & Haber, D. A. (2007) Cell 131, 1097-108; Hock, J. & Meister, G. (2008) Genome Biol 9, 210; Su, H., et al. (2009) Genes Dev 23, 304-17). Since duplex RNA is the trigger for both RNAa and RNAi, PC-3 cells were transfected with siRNAs targeting Ago1-4 (siAgo1, siAgo2, siAgo3, or siAgo4) in combination with dsEcad-215 or siMOF to compare the functional role of each Ago family member on RNAa and RNAi activity, respectively. As shown in FIG. 2A, the expression of each Ago family member was knocked down by its corresponding siRNA; however, only siAgo2 completely prevented E-cadherin induction. This is consistent with previous reports that selective knockdown of Ago2 also prevented dsP21-322 activity (Li, L. C., et al. (2006) Proc Natl Acad Sci USA 103, 17337-42). Since Ago2 is the catalytic core to conventional RNAi (Meister, G., et al. (2004) Mol Cell 15, 185-97), depletion of Ago2 also abolished the RNAi-mediated knockdown of MOF transcript (FIG. 2B). Taken together, this data suggests that Ago2 is a conserved factor required by both RNAa and RNAi.

Strand Modifications to Manipulate RNAa Activity.

Modification to the 5'-terminus of the guide strand in duplex RNAs can have variable effects on small RNA-guided mechanisms. For instance, 5'-modification to siRNA duplexes is known to interfere with RNAi activity (Chiu, Y. L. & Rana, T. M. (2002) Mol Cell 10, 549-61; Chen, P. Y., et al. (2008) Rna 14, 263-74), while modification to the 5'-termini in duplex RNAs involved in directing transcriptional gene silencing (TGS) retain function (Weinberg, M. S., et al. (2006) Rna 12, 256-62; Han, J., et al. (2007) Proc Natl Acad Sci USA 104, 12422-7). Therefore, experiments were performed to determine if blocking the 5'-termini in saRNA molecules modulates RNAa activity. Modified saRNA molecules were synthesized that were derived from dsEcad-215 and dsP21-322 and covalently linked to biotin at either the 5'-end of the antisense (dsRNA-AS-5'Bio) or sense (dsRNA-S-5'Bio) strand (FIG. 3A). As shown in FIG. 3B, transfection of dsEcad-215 modified at its 5'-end of the antisense strand (dsEcad-215-AS-5'Bio) completely blocked induction of E-cadherin, while 5'-modification to the sense strand (dsEcad-215-S-5'Bio) retained RNAa activity. Likewise, dsP21-322-AS-5'Bio abolished activation of p21, while dsP21-322-S-5'Bio induced p21 levels equivalent to unmodified dsP21-322 (FIG. 3C).

Selection of the guide strand in RNAi is determined by the terminal thermodynamic characteristics within siRNA molecules. The strand with lower thermodynamic stability at its 5'-end is preferentially loaded into Ago2 to become the guide strand (Khvorova, A., et al. (2003) Cell 115, 209-16). Given that RNAa is also dependent on Ago2, modified saRNA molecules were synthesized that possessed mismatched bases opposite the 5' most nucleotide of either the antisense (dsRNA-AS-MM) or sense (dsRNA-S-MM) strand (FIG. 3D). Presumably, the intentional mismatch would lower the thermodynamic stability of the 5'-terminus at either strand and forcibly select the strand with the mismatch as the guide strand. As shown in FIG. 3E, transfection of dsEcad-215 with a mismatch at the 5'-end of the antisense strand (dsEcad-215-AS-MM) resulted in robust increase in transcriptional activity, while no additional transcriptional activity was observed with the 5' mismatch of the sense strand (dsEcad-215-S-MM). Similarly, dsP21-322-AS-MM enhanced p21 expression, while dsP21-322-S-MM sequestered RNAa activity (FIG. 3F). It is also important to note that mismatches at the 5'-end of the antisense strand of both dsEcad-215 (dsEcad-215-AS-MM) and dsP21-322 (dsP21-322-AS-MM) further enhanced RNA activity (FIG. 3E-F).

Interestingly, dsP21-322-S-MM possessed some residual RNAa function (FIG. 3F). To determine if the remaining RNAa activity may have resulted from the sense strand, a modified dsP21-322 molecule was synthesized that possessed both a mismatch at the 5'-end of the sense strand and a biotin modification at the 5'-terminus of the antisense strand to forcibly load the sense strand and block any residual activity of the antisense strand, respectively (FIG. 3G). As shown in FIG. 3H, transfection of the modified dsP21-322 molecule (dsP21-322-AS-5'Bio-S-MM) completely suppressed p21 gene activation. Utilizing both modifications in combination clearly defined strand function in dsP21-322; the antisense strand of dsP21-322 is responsible for RNAa activity. As such, the residual activity of dsP21-322-S-MM most likely resulted from the occasional selection of the antisense strand to guide p21 activation.

Modifying the 2'-sugar in siRNA molecules is known to increase endonuclease resistance and abrogate immune stimulation (Layzer, J. M., et al. (2004) Rna 10, 766-71; Czauderna, F., et al. (2003) Nucleic Acids Res 31, 2705-16; Sioud, M., et al. (2007) Biochem Biophys Res Commun 361, 122-6). In order to determine the tolerance of saRNA molecules to 2'-sugar modification, two dsP21-322 variants were designed that contained 2'-O-methyl (2'-OMe) modifications in either the sense (dsP21-322-S-2'OMe) or antisense (dsP21-322-AS-2'OMe) strand. As shown in FIG. 4A-B, 2'-OMe modification within the sense strand suppressed RNAa activity of dsP21-322; p21 induction by dsP21-322-S-2'OMe was ~50% less than dsP21-322 or dsP21-322-AS-2'OMe in both PC-3 and HeLa cells. This data suggests that excessive modification to the 2'-sugar of the passenger strand in saRNA molecules may interfere with RNAa activity.

To determine if modification of the 3'-termini within saRNA interferes with RNAa activity, dsEcad-215 was synthesized with biotin linked to the 3'-end of both the sense and antisense strands (dsEcad-215-3'Bio; FIG. 4C). As shown in FIG. 4D-E, transfection of dsEcad-215-3'Bio still induced the expression of E-cadherin. This data indicates that saRNA modified at the 3'-termini retain RNAa activity.

Exploiting saRNA Modifications to Optimize RNAa Function.

Improper selection of the passenger strand in saRNA duplexes may lead to off-target effects by interacting with non-specific transcripts or gene promoters complementary to the passenger strand. In order to optimize RNAa activity and suppress the theoretical off-target effects of the passenger strand, dsEcad-215 was designed and synthesized to possess a blocked 5'-terminus on the sense strand and a mismatched base opposite the 5' most nucleotide of the antisense strand (dsEcad-215-S-5'Bio-AS-MM) to suppress sense strand activity and enhance selection of the antisense strand, respectively (FIG. 5A). Transfection of dsEcad-215-S-5'Bio-AS-MM readily induced E-cadherin expression with increased activity similar to dsEcad-215-AS-MM, while dsEcad-215-S-5'Bio matched levels achieved by unmodified dsEcad-215 (FIG. 5B-C).

In order to validate reduced off-target effects caused by selection of the sense strand, a target site was cloned complementary to the sense strand into a luciferase reporter vector (pOffTar-luc) and quantified luciferase activity in the presence of several modified dsEcad-215 molecules. As shown in FIG. 5D, dsEcad-215 resulted in reduced luciferase activity of pOffTar-luc, while the activity of a non-specific luciferase reporter construct (pNonSpec-luc) was not altered by saRNA treatment. dsEcad-215-S-MM served as a positive control since the mismatched base present in the duplex would forcibly enhance sense strand selection and subsequent off-target activity. The reduction in pOffTar-luc activity by dsEcad-215 and dsEcad-215-S-MM confirms the off-target potential of the sense strand. However, modified saRNAs (dsEcad-S-5'Bio, dsEcad-215-AS-MM, and dsEcad-215-S-5'Bio-AS-MM) caused luciferase activity of pOffTar-luc to rebound demonstrating inhibition of off-target function (FIG. 5E). Overall, dsEcad-215-S-5'Bio-AS-MM possessed both enhanced RNAa activity toward E-cadherin expression and inhibition of non-specific function of the sense strand. This data indicates that functional modifications to saRNA molecules can be utilized to both enhance RNAa activity and reduce non-specific off-target effects.

Discussion

The optimal window of RNAa activity was delayed by ~24-48 hours in comparison to RNAi. Perhaps, the delay in RNAa activity reflects a more complicated mechanism with additional rate-limiting steps. In nematode, a special ribonucleoprotein is required to shuttle small siRNAs into nuclei in order to facilitate nuclear RNAi (Guang, S., et al. (2008) Science 321, 537-41). Although this protein is not conserved in humans, cytoplasmic miRNA has been shown to actively migrate into the nuclear fraction of living human cells (Foldes-Papp, Z., et al. 2009) Curr Pharm Biotechnol 10, 569-78. Because RNAa is a nuclear process acting on gene transcription, acquiring access to the nucleus may serve as an additional rate-limiting step for RNAa. Changes in chromatin structure are also associated with RNAa (Janowski, B. A., et al. (2007) Nat Chem Biol 3, 166-73; Li, L. C., et al. (2006) Proc Natl Acad Sci USA 103, 17337-42; Turunen, M. P., et al. (2009) *Circ Res* 105, 604-9), which may further contribute to the delayed kinetics. Regardless, identifying the delay and defining the optimal window of RNAa activity allows for proper assessment for gene induction and functional analysis of saRNAs. Assessing the rate of RNAa activity in cell culture also gives insight into the anticipated in vivo pharmacological properties of RNAa. For instance, RNAa-based drugs may require several days before target gene induction or beneficial changes in phenotype are evident. Moreover, the longer-lasting effect of RNAa may result in less frequent administration of saRNA; a potential benefit as duplex RNA in excess can have toxic consequences (Grimm, D., et al. (2006) Nature 441, 537-41).

Identifying features and key factors involved in the RNAa pathway can influence saRNA design. As such, defining Ago2 as an important mechanistic component implicated that chemically-modified saRNAs may function to manipulate RNAa activity. Utilizing dsP21-322 and dsEcad-215 as functional examples of saRNA molecules revealed that blocking the 5'-end or incorporating intentional mismatches can determine strand function. Studies have revealed an abundance of sense and antisense transcription within the promoters and flanking regions of active genes (Seila, A. C., et al. (2008) Science 322, 1849-51; Core, L. J., Waterfall, J. J. & Lis, J. T. (2008) Science 322, 1845-8; Preker, P., et al. (2008) Science 322, 1851-4). Furthermore, overlapping noncoding RNAs and upstream cryptic transcripts have been shown to play substantial roles in regulating gene expression (Goodrich, J. A. & Kugel, J. F. (2009) Crit Rev Biochem Mol Biol 44, 3-15; He, Y., et al. (2008) Science 322, 1855-7; Katayama, S., et al. (2005) Science 309, 1564-6; Petruk, S., et al. (2006) Cell 127, 1209-21; Martens, J. A., et al. (2004) Nature 429, 571-4). As such, models for RNAa have included saRNAs targeting antisense transcripts and/or promoter-derived sequences to facilitate gene activation (Li, L. C., et al. (2006) Proc Natl Acad Sci USA 103, 17337-421; Place, R. F., et al. (2008) Proc Natl Acad Sci USA 105, 1608-13; Kuwabara, T., et al. (2004) Cell 116, 779-93; Wang, X., et al. (2008) Nature 454, 126-30; Morris, K. V., et al. (2008) PLoS Genet 4, e1000258;

Schwartz, J. C., et al. (2008) Nat Struct Mol Biol 15, 842-8). RNAs transcribed in sense and antisense orientations have already been shown to serve as docking sites for transcriptional gene silencing (TGS) mediated by small duplex RNAs (Han, J., et al. (2007) Proc Natl Acad Sci USA 104, 12422-7; Mahmoudi, S., et al. (2009) Mol Cell 33, 462-71; Gonzalez, S., et al. (2008) Cell Cycle 7, 2601-8). Likewise, nascent sense and antisense transcripts may both serve as the targets for RNAa, as well. Utilizing modified saRNAs can not only improve mechanistic studies by defining strand activity, but also assist in determining orientation of such putative target transcripts.

Identifying functional modifications is also necessary for therapeutic development in order to improve the medicinal properties of saRNAs. In the case of dsP21-322 and/or dsEcad-215 (i) blocking the 5'-end of the sense strand completely inhibited its potential off-target effects; (ii) incorporating an intentional mismatch opposite the 5' most nucleotide in the antisense strand enhanced target gene induction, as well as reduced the off-target activity generated by the sense strand; (iii) 2'Ome modification to the sense strand inhibited RNAa activity, while the same modification to the antisense strand did not interfere with gene induction; (iv) modifying the 3'-end of either the sense or antisense strand had minimal effects on RNAa activity. Although the preferred guide strand may vary between the sense or antisense strand in different saRNAs, each modification may still be applied to manipulate saRNA activity or define strand function. As such, extrapolating these modifications to fit other saRNAs based on strand activity will also improve their medicinal properties.

Development of saRNAs for therapeutic application may also require multiple modifications to optimize medicinal benefits. For instance, we were able to enhance dsEcad-215 activity by blocking both the 5'-end of the sense strand and incorporating a mismatch opposite the 5' most nucleotide of the antisense strand. The combination of both modifications alleviated any potential off-target effects that would arise from improper use of the sense strand and enhanced gene induction; features needed to manipulate in order to develop RNAa therapeutics. Modification to the sugar s of the sense and antisense backbones (i.e. 2'-OMe, 2'-flouro, etc.) in saRNA duplexes may also improve therapeutic application by increasing endonuclease resistance and serum stability, much as they are utilized to stabilize siRNAs, as long as the passenger strand is devoid of inhibitory modifications. Tethering small molecules (i.e. cholesterol) to the 3'-ends of saRNAs could also be used to improve systemic delivery of RNAa-based drugs. Conjugation of other compounds (i.e. flurogenic labels) to the 3'-termini may be effective at providing visual confirmation of saRNA uptake into target cells or tissue, as well.

RNAi is rapidly developing into a promising new approach for combating disease at the genetic level; however, it can only provide antagonism of specific molecular targets. By utilizing saRNAs as therapeutic compounds, RNAa offers similar benefits as RNAi, while facilitating the exact opposite response—gene activation. This approach addresses a missing void in RNA-based gene therapies and offers a novel solution to provide greater efficacy in disease control. RNAa has already been shown to activate genes capable of suppressing cancer cell growth (e.g. p21, E-cadherin, p53, NKX3.1, etc.), triggering angiogenesis (e.g. VEGF), or influencing stem cell maintenance (e.g. CXCR4) (Li, L. C., et al. (2006) Proc Natl Acad Sci USA 103, 17337-42; Chen, Z., et al. (2008) Mol Cancer Ther 7, 698-703; Turunen, M. P., et al. (2009) Circ Res 105, 604-9; Huang, V., et al. PLoS One 5, e8848). As such, the ability to selectively up-regulate genes acting against a disease state can have far-reaching impacts in almost every therapeutic realm. However, application of RNAa is not limited to only cancer therapeutics. RNAa also has potential to function as a surrogate tool for vector-based gene overexpression systems. RNAa offers a new approach to enhance endogenous gene expression that may be manipulated to target a variety of genes. As momentum within the biological sciences increases, RNAa may become an important technique to augment gene expression for therapeutics and functional gene studies.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for increasing the expression of a p21 gene in a cell, the method comprising:
   introducing into a cell an effective amount of a modified p21 gene-specific small activating RNA (saRNA), the modified p21 gene-specific saRNA comprising:
   i. an antisense strand comprising a mismatch at the 5' terminal nucleotide compared to antisense strand of a p21 gene-specific control saRNA; and
   ii. a sense strand of the p21 gene-specific control saRNA, the sense strand comprising a blocking moiety at the 5' terminus;
   wherein the expression of the p21 gene is increased, wherein the increase in expression of the p21 gene by introduction of said modified gene-specific saRNA is greater than the increase in expression of a gene following administration of said p21 gene-specific control saRNA, and the off-target effects of the modified p21 gene-specific saRNA are less than the off-target effects following introduction of said p21 gene-specific control saRNA, wherein the sense and antisense strands form a duplex region of between 15 to 30 base pairs in the modified saRNA molecule.

2. The method according to claim 1, wherein said modified saRNA molecule is introduced into the cell by expression from a nucleic acid vector.

3. The method according to claim 1, wherein said modified saRNA molecule is introduced to the cell as an RNA molecule.

4. The method according to claim 1, wherein said control saRNA comprises a sense strand comprising the sequence SEQ ID NO:17 and an antisense strand comprising the sequence SEQ ID NO:18.

5. The method according to claim 1, wherein said modified saRNA comprises a sense strand comprising the sequence SEQ ID NO:27.

6. The method according to claim 1, wherein said modified saRNA comprises a sense strand comprising the sequence SEQ ID NO:23.

7. The method according to claim 1, wherein said modified saRNA comprises a sense strand comprising the sequence SEQ ID NO:33.

8. A method of reducing proliferation of a cell in a subject having a cellular proliferative disease, the method comprising:
   administering to said subject an effective amount of a modified small activating RNA (saRNA) molecule that is specific for a p21 gene that suppresses cell proliferation, said modified small activating RNA (saRNA) comprising:
   i. an antisense strand comprising a mismatch at the 5' terminus compared to antisense strand of a control saRNA that is specific for said p21 gene; and
   ii. a sense strand of the p21 gene-specific control saRNA, the sense strand comprising a blocking moiety at the 5' terminus,
   wherein the administering provides for an increase in expression of said p21 gene, wherein cellular proliferation is decreased wherein the increase in expression of the p21 gene following administration of said modified saRNA is greater than the increase in expression of the gene following administration of said control saRNA, and the off-target effects of the modified p21 gene-specific saRNA are less than the off-target effects following administration of said p21 gene-specific control saRNA, wherein the sense and antisense strands form a duplex region of between 15 to 30 base pairs in the modified saRNA molecule.

9. The method of claim 8, wherein the antisense strand of the saRNA is complementary to a non-coding nucleic acid sequence of p21 gene.

10. The method of claim 9, wherein the non-coding nucleic acid sequence is a nucleic acid sequence in promoter region of p21 gene.

11. The method of claim 8, wherein the saRNA is 19-21 base pairs in length.

12. The method of claim 8, wherein the sense and antisense strands form a duplex region of 18 base pairs in the modified saRNA molecule.

13. The method of claim 10, wherein the saRNA is 19-21 base pairs in length.

14. The method of claim 13, wherein the sense and antisense strands form a duplex region of 18 base pairs in the modified saRNA molecule.

15. The method of claim 8, wherein said control saRNA comprises a sense strand comprising the sequence SEQ ID NO:17 and an antisense strand comprising the sequence SEQ ID NO:18.

16. The method of claim 8, wherein said modified saRNA comprises a sense strand comprising the sequence SEQ ID NO:27.

17. The method of claim 8, wherein said modified saRNA comprises a sense strand comprising the sequence SEQ ID NO:23.

18. The method of claim 8, wherein said modified saRNA comprises a sense strand comprising the sequence SEQ ID NO:33.

19. The method of claim 1, wherein the antisense strand of the saRNA is complementary to a non-coding nucleic acid sequence of p21 gene.

20. The method of claim 1, wherein the non-coding nucleic acid sequence is a nucleic acid sequence in promoter region of p21 gene.

21. The method of claim 1, wherein the saRNA is 19-21 base pairs in length.

22. The method of claim 1, wherein the sense and antisense strands form a duplex region of 18 base pairs in the modified saRNA molecule.

23. The method of claim 20, wherein the saRNA is 19-21 base pairs in length.

24. The method of claim 23, wherein the sense and antisense strands form a duplex region of 18 base pairs in the modified saRNA molecule.

25. The method of claim 1, wherein the blocking moiety is present at the 5' terminal nucleotide.

26. The method of claim 8, wherein the blocking moiety is present at the 5' terminal nucleotide.

* * * * *

SEQUENCE LISTING

```
<160> NUMBER OF SEQ ID NOS: 55

<210> SEQ ID NO 1
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 1
gugauccagu cucgagugau u                                              21

<210> SEQ ID NO 2
```

```
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 2
ucacucgaga cuggaucacu u                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 3
uggacucuuc ggagaacuut t                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 4
aaguucuccg aagaguccat t                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 5
gagaagaggu gcucaagaat t                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 6
uucuugagca ccucuucuct t                                              21

<210> SEQ ID NO 7
<211> LENGTH: 21
<212> TYPE: DNA
<213> ORGANISM: Artificial Sequence
```

```
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 7
gcacggaagu ccaucugaat t                                                   21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 8
uucagaugga cuuccgugct t                                                   21

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 9
gaaauuagca gauugguaat t                                                   21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 10
uuaccaaucu gcuaauuuct t                                                   21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 11
ggccagaacu aauagcaaut t                                                   21

<210> SEQ ID NO 12
<211> LENGTH: 21
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 12
auugcuauua guucuggcct t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 13
uucuccgaac gugucacgut t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 14
acgugacacg uucggagaat t                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 15
aaccgugcag gucccauaat t                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 16
uuaugggacc ugcacgguut t                                              21

<210> SEQ ID NO 17
<211> LENGTH: 21
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 17
ccaacucauu cuccaaguat t                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 18
uacuuggaga augaguuggt t                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 19
acuacugagu gacaguagat t                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 20
ucuacuguca cucaguagut t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: misc_difference
<222> LOCATION: 1
<223> OTHER INFORMATION: biotinylated A

<400> SEQUENCE: 21
```
aaccgugcag gucccauaat t                    21

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: misc_difference
<222> LOCATION: 1
<223> OTHER INFORMATION: biotinylated U

<400> SEQUENCE: 22
uuaugggacc ugcacgguut t                    21

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: misc_difference
<222> LOCATION: 1
<223> OTHER INFORMATION: biotinylated C

<400> SEQUENCE: 23
ccaacucauu cuccaaguat t                    21

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: misc_difference
<222> LOCATION: 1
<223> OTHER INFORMATION: biotinylated U

<400> SEQUENCE: 24
uacuuggaga augaguuggt t                    21

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 25
aaccgugcag gucccauaut t                    21

-continued

```
<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 26
uacuuggaga augaguugct t                                             21

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA

<400> SEQUENCE: 27
ccaacucauu cuccaaguut t                                             21

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: modified_base
<222> LOCATION: 8
<223> OTHER INFORMATION: m2a
<220> FEATURE:
<221> NAME/KEY: modified_base
<222> LOCATION: 9
<223> OTHER INFORMATION: um

<400> SEQUENCE: 28
ccaacucauu cuccaaguat t                                             21

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: modified_base
<222> LOCATION: 8
<223> OTHER INFORMATION: m2a
<220> FEATURE:
<221> NAME/KEY: modified_base
<222> LOCATION: 9
<223> OTHER INFORMATION: gm

<400> SEQUENCE: 29
uacuuggaga augaguuggt t                                             21
```

```
<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: misc_difference
<222> LOCATION: 21
<223> OTHER INFORMATION: biotinylated dT

<400> SEQUENCE: 30
aaccgugcag gucccauaat t                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: misc_difference
<222> LOCATION: 21
<223> OTHER INFORMATION: biotinylated dT

<400> SEQUENCE: 31
uuaugggacc ugcacgguut t                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: misc_difference
<222> LOCATION: 1
<223> OTHER INFORMATION: biotinylated a

<400> SEQUENCE: 32
aaccgugcag gucccauaut t                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: misc_difference
<222> LOCATION: 1
<223> OTHER INFORMATION: biotinylated C

<400> SEQUENCE: 33
ccaacucauu cuccaaguut t                                              21
```

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
cctgggactc cacctacaga                                            20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
ggatgacaca gcgtgagaga                                            20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
gcccagtgga cagcgagcag                                            20

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 37
gccggcgttt ggagtggtag a                                          21

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
atccacatcg ggaactacga                                            20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
tctttgccat caacttcgtg                                            20

<210> SEQ ID NO 40
<211> LENGTH: 22
<212> TYPE: DNA
<213> ORGANISM: Artificial Sequence
<220> FEATURE:

<223> OTHER INFORMATION: Synthetic oligonucleotide

<400> SEQUENCE: 40
catctatgac atcaccaacg tc                                      22

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 41
gctttgatca ccataaccat ct                                      22

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
gcgaattggg aagagtggta                                         20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
gcaggtgctg ggatagagac                                         20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
cgcgtccgaa ggctgctcta                                         20

<210> SEQ ID NO 45
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 45
tggctgtgcc ttgtaaaacg ct                                      22

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
atcccagctg gaacaacagt                                         20

```
<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
gcgtacgtaa gtgtggcaga                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
gggtagggaa aagtggcaat                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
gagcgagtgc acctcacata                                               20

<210> SEQ ID NO 50
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 50
tcccatcacc atcttcca                                                 18

<210> SEQ ID NO 51
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 51
catcacgcca cagtttcc                                                 18

<210> SEQ ID NO 52
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 52
ctagtagatc ttgtgtgtgt gttatgggac ctgcacggtt gaacatacac a            51

<210> SEQ ID NO 53
<211> LENGTH: 51
<212> TYPE: DNA
<213> ORGANISM: Artificial Sequence
<220> FEATURE:
<223> OTHER INFORMATION: Synthetic oligonucleotide
```

-continued

```
<400> SEQUENCE: 53
agcttgtgta tgttcaaccg tgcaggtccc ataacacaca cacaagatct a                51

<210> SEQ ID NO 54
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 54
ctagtagatc ttgtgtgtgt gggtaggcgt caagtagata gcgaacatac aca              53

<210> SEQ ID NO 55
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 55
agcttgtgta tgttcgctat ctacttgacg cctacccaca cacacaagat cta              53
```